United States Patent
Gul-Uludag et al.

(10) Patent No.: US 12,264,333 B2
(45) Date of Patent: Apr. 1, 2025

(54) COLOSTRUM DERIVED STEM CELLS, NEURAL DIFFERENTIATION, COMPOSITIONS AND SUPPLEMENTS FOR ENHANCING MAMMALIAN HEALTH

(71) Applicant: MyStem Biotechnologies Inc., Edmonton (CA)

(72) Inventors: Dilruba Hilal Gul-Uludag, Edmonton (CA); Robert Edward Burrell, Sherwood Park (CA)

(73) Assignee: MyStem Biotechnologies Inc., Edmonton (CA)

(*) Notice: Subject to any disclaimer, the term of this patent is extended or adjusted under 35 U.S.C. 154(b) by 891 days.

(21) Appl. No.: 17/274,404

(22) PCT Filed: Sep. 20, 2019

(86) PCT No.: PCT/CA2019/051343
§ 371 (c)(1),
(2) Date: Mar. 8, 2021

(87) PCT Pub. No.: WO2020/056521
PCT Pub. Date: Mar. 26, 2020

(65) Prior Publication Data
US 2021/0269769 A1 Sep. 2, 2021

Related U.S. Application Data

(60) Provisional application No. 62/734,127, filed on Sep. 20, 2018.

(51) Int. Cl.
| | | |
|---|---|---|
| C12N 5/074 | (2010.01) | |
| A61K 35/28 | (2015.01) | |
| A61K 35/30 | (2015.01) | |
| C12N 5/079 | (2010.01) | |
| C12N 5/0793 | (2010.01) | |

(52) U.S. Cl.
CPC ............ *C12N 5/0607* (2013.01); *A61K 35/28* (2013.01); *A61K 35/30* (2013.01); *C12N 5/0619* (2013.01); *C12N 5/0622* (2013.01); *C12N 2501/998* (2013.01); *C12N 2506/03* (2013.01)

(58) Field of Classification Search
None
See application file for complete search history.

(56) References Cited

U.S. PATENT DOCUMENTS

| | | |
|---|---|---|
| 7,229,827 B2 | 6/2007 | Kim et al. |
| 7,776,586 B2 | 8/2010 | Cregan et al. |
| 9,085,755 B2 | 7/2015 | Phan et al. |
| 9,464,270 B2 | 8/2016 | Kakulas et al. |
| 9,492,512 B2 | 11/2016 | Bartorelli et al. |
| 9,943,597 B2 | 4/2018 | Llan et al. |
| 2013/0108587 A1 | 5/2013 | Drapeau et al. |
| 2014/0004205 A1 | 1/2014 | Satyaraj |
| 2014/0134140 A1 | 5/2014 | Caplan et al. |
| 2016/0000710 A1 | 1/2016 | Gupta et al. |
| 2018/0051249 A1 | 2/2018 | Hingtgen et al. |

FOREIGN PATENT DOCUMENTS

| | | |
|---|---|---|
| JP | 2015506931 A | 3/2015 |
| WO | WO 2013/098333 A1 | 7/2013 |
| WO | WO 2017/134559 A1 | 8/2017 |
| WO | WO 2017/139638 A1 | 8/2017 |

OTHER PUBLICATIONS

Lee SC, Jeong HJ, Lee SK, Kim SJ. Lipopolysaccharide preconditioning of adipose-derived stem cells improves liver-regenerating activity of the secretome. Stem Cell Res Ther. Apr. 14, 2015;6(1):75. doi: 10.1186/s13287-015-0072-7. PMID: 25890074; PMCID: PMC4416308. (Year: 2015).*

Werner-Misof, C., Pfaffl, M. W., & Bruckmaier, R. M. (2007). Dose-dependent immune response in milk cells and mammary tissue after intramammary administration of lipopolysaccharide in dairy cows. Veterinarni Medicina, 52(6), 231-244. (Year: 2007).*

Stabel JR. Pasteurization of colostrum reduces the incidence of paratuberculosis in neonatal dairy calves. J Dairy Sci. Sep. 2008;91(9):3600-6. doi: 10.3168/jds.2008-1107. PMID: 18765618. (Year: 2008).*

(Continued)

*Primary Examiner* — Allison M Fox
*Assistant Examiner* — Qinhua Gu
(74) *Attorney, Agent, or Firm* — Leydig, Voit & Mayer, Ltd.

(57) ABSTRACT

The invention provides colostrum derived stem cell populations, compositions and supplements having antimicrobial properties for enhancing mammalian health and for treating or preventing microbial contamination or infection. Also provided are methods of producing these populations, compositions and supplements from a female mammal in an inflammatory state. Also provided are colostrum derived stem cell populations and method of inducing differentiation into neural cells in neural progenitor medium including mammalian cell culture medium supplemented with casein depleted fraction of whey derived from colostrum. Also provided are neural progenitor medium, population of in vitro differentiated neural cells and pharmaceutical compositions containing same for use in treating neurological disease or disorder.

17 Claims, 14 Drawing Sheets

(56) References Cited

OTHER PUBLICATIONS

Chae et al. "Bovine colostrum demonstrates anti-inflammatory and antibacterial activity in in vitro models of intestinal inflammation and infection" Journal of Functional Foods 28 (2017), pp. 293-298.
European Search Report in corresponding European Application 19862184.9, mailed May 11, 2022.
Ti et al. "LPS-preconditioned mesenchymal stromal cells modify macrophage polarization for resolution of chronic inflammation via exosome-shuttled let-7b" J Transl Med 13:308 (2015), 14 pp.
Abd Allah et al. "Breast milk MSCs: An explanation of tissue growth and maturation of offspring" IUBMB Life, 2016, vol. 68, No. 12, pp. 935-942.
Alcayaga-Miranda et al., "Antimicrobial Activity of Mesenchymal Stem Cells: Current Status and New Perspectives of Antimicrobial Peptide-Based Therapies" Front Immunol, 2017, vol. 8, pp. 339.
Anghileri et al. "Neuronal differentiation potential of human adipose-derived mesenchymal stem cells" Stem Cells Dev, 2008, vol. 17, No. 5, pp. 909-916.
Aydin et al. "Transfer and Integration of Breast Milk Stem Cells to the Brain of Suckling Pups" Nature Scientific Reports, 2018, 8:14289 pp. 1-9.
Banfi et al. "Proliferation kinetics and differentiation potential of ex vivo expanded human bone marrow stromal cells: Implications for their use in cell therapy" Exp Hematol, 2000, vol. 28, No. , pp. 707B715.
Bernardo et al., "Mesenchymal stromal cells: sensors and switchers of inflammation" Cell Stem Cell, 2013, vol. 13, No. 4, pp. 392-402.
Boxall et al. "Markers for characterization of bone marrow multipotential stromal cells" Stem Cells Int, 2012, vol. 2012, 975871.
Cacho et al. "Innate Immunity and Breast Milk" Frontiers in Immunology, 2017, vol. 8, Art. 584, pp. 1-10.
Caplan, Arnold. "All MSCs Are Pericytes?" Cell Stem Cell 3, Sep. 11, 2008, pp. 229-230.
Dillingh et al. "Characterization of inflammation and immune cell modulation induced by low-dose LPS administration to healthy volunteers" Journal of Inflammation, 2014, 11:28.
Eggenhofer et al., "The Life and Fate of Mesenchymal Stem Cells" Front Immunol, 2014, vol. 19, No. 5, pp. 148.
Fan et al., "Unravelling the mystery of stem/progenitor cells in human breast milk" PLoS One, 2010, vol. 5, No. 12, pp. e14421.
Friedenstein et al., "Precursors for fibroblasts in different populations of hematopoietic cells as detected by the in vitro colony assay method" Exp. Hematol, 1974, vol. 2, No. 2, pp. 83-92.
Hassiotou et al. "At the Dawn of a New Discovery: The Potential of Breast Milk Stem Cells, Adv. Nutr." 2014, 5: 770-778.
Hassiotou et al. "Breastmilk is a Novel Source of Stem Cells with Multilineage Differentiation Potential", Stem Cells, 2012, 30, pp. 2164-2174.
Hosseini et al. "A Differentiation of human breast-milk stem cells to neural stem cells and neurons" Neurol Res Int, 2014;2014:807896.
Hsieh et al. "AIGF-I instructs multipotent adult neural progenitor cells to become oligodendrocytes" J Cell Biol, 2004, vol. 164, No. 1, pp. 111B122.
Huat et al. "AIGF-1 enhances cell proliferation and survival during early differentiation of mesenchymal stem cells to neural progenitor-like cells" BMC Neurosci. 2014;15:91.
International Preliminary Report on Patentability issued Mar. 23, 2021 for International Application PCT/CA2019/051343.
International Search Report and Written Opinion issued Dec. 10, 2019 for International Application PCT/CA2019/051343.
Kaingade et al. "Assessment of Growth Factors Secreted by Human Breastmilk Mesenchymal Stem Cells, Breastfeeding Medicine" 2016, vol. 11, No. 1, pp. 26-31.
Kaingade et al. "Cellular Components, Including Stem-Like Cells, of Preterm Mothers Mature Milk as Compared with Those in Her Colostrum: A Pilot Study" Breastfeeding Medicine, 2017, vol. 12, No. 7, pp. 1-11.
Kakulas et al. "Breastmilk is Unlikely to be a Source of Mesenchymal Stem Cells" Breastfeeding Medicine, 2016, vol. 11, No. 3, pp. 150-151.
Krasnodembskaya et al. "Antibacterial Effect of Human Mesenchymal Stem Cells Is Mediated in Part from Secretion of the Antimicrobial Peptide LL-37" Stem Cells, 2010, vol. 28, No. 12, pp. 2229B2238.
Kumar et al. "Human Colostrum is a Rich Source of Cells with Stem Cell-Like Properties" J of Basic, Clinical & Applied Health Sciences, 2017, vol. 1, Issue 1, pp. 26-31.
Landers et al. "A Review of Antibiotic Use in Food Animals: Perspective, Policy, and Potential, Public Health Rep" 2012, vol. 127, No. 1, pp. 4B22.
Le Blanc et al. "AImmunobiology of human mesenchymal stem cells and future use in hematopoietic stem cell transplantation" Biol Blood Marrow Transplant, 2005, vol. 11, No. 5, pp. 321-334.
Marquez-Curtis et al. "Mesenchymal stromal cells derived from various tissues: Biological, clinical and cryopreservation aspects" Cryobiology, 2015, vol. 71, No. 2, pp. 181B197.
McDonald et al. "Transplanted embryonic stem cells survive, differentiate and promote recovery in injured rat spinal cord" Nat Med, 1999, vol. 5, No. 12, pp. 1410-1413.
Muraglia et al. "Clonal mesenchymal progenitors from human bone marrow differentiate in vitro according to a hierarchical model" J Cell Sci 2000, vol. 113 , pp. 1161B1166.
Murphy et al. "Mesenchymal stem cells: environmentally responsive therapeutics for regenerative medicine", Experimental & Mol. Medicine, 2013, 45, e54, pp. 1-16.
Patki et al. "Human breast milk is a rich source of multipotent mesenchymal stem cells" Hum Cell, 2010, vol. 23, No. 2, pp. 35-40.
Pichiri et al. "Human breast milk stem cells: a new challenge for perinatologists" J. of Pediatric and Neonatal Individ. Medicine, 2016, 5(1):e050120, pp. 1-7.
Pipino et al., "Identification and Characterization of a Stem Cell-Like Population in Bovine Milk: A Potential New Source for Regenerative Medicine in Veterinary" Stem Cells and Development, 2018, vol. 27, No. 22, pp. 1-19.
Ramirez et al., "Bovine Colostrum or Milk as a Serum Substitute for the Cultivation of a Mouse Hybridoma, Biotech. and Bioeng." 1990, vol. 35, pp. 882-889.
Sani et al., "Origins of the breast milk-derived cells; an endeavor to find the cell sources" Cell Biol Int, 2015, vol. 39, No. 5, pp. 611-618.
Steimer et al. "Serum-free growth of normal and transformed fibroblasts in milk: differential requirements for fibronectin" J Cell Biol, 1981 Vol. 88, No. 2, pp. 294-300.
Steimer et al. "The serum-free growth of cultured cells in bovine colostrum and in milk obtained later in the lactation period" J Cell Physiol, 1981, vol. 109, No. 2, pp. 223-234.
Sutton et al. "Antimicrobial Properties of Mesenchymal Stem Cells: Therapeutic Potential for Cystic Fibrosis Infection, and Treatment", Stem Cells Int, 2016, 2016: 5303048.
Thapa, B. R. "Health factors in colostrum" Indian J Pediatr, 2005, vol. 72, No. 7, pp. 579-581.
Ullah et al. "Human mesenchymal stem cells—current trends and future prospective" Biosci Rep, 2015, vol. 35, No. 2, pp. e00191.
Whitfield et al. "Onset of heterogeneity in culture-expanded bone marrow stromal cells" Stem Cell Res, 2013, vol. 11, No. 3, pp. 1365-1377.
Woodbury et al. "Adult rat and human bone marrow stromal cells differentiate into neurons" J Neuro Res, 2000, vol. 61, No. 4, pp. 364B370.
Yarak et al. "Human adipose-derived stem cells: current challenges and clinical perspectives" An Bras Dermatol, 2010, vol. 85, No. 5, pp. 647-656.
Zhao et al. "Effects of IGF-1 on neural differentiation of human umbilical cord derived mesenchymal stem cells" Life Sciences, 2016, vol. 151, No. 15, pp. 93-101.
EPC Communication pursuant to Article 94(3) mailed Aug. 8, 2024, in corresponding European Application No. 19 862 184.9, 4 pages.
Chouaib et al. (2023) "Towards the Standardization of Mesenchymal Stem Cell Secretome-Derived Product Manufacturing for Tissue Regeneration," Int. J. Mol. Sci. 24: 12594.

(56) References Cited

OTHER PUBLICATIONS

Office Action mailed Jun. 26, 2024 in corresponding Canadian Application No. 3,110,909, 4 pages.
Extended European Search Report mailed Aug. 18, 2022 in corresponding European Application No. 19862184.9-1118, 11 pages.
Office Action mailed Oct. 16, 2023 in corresponding Canadian Application No. 3,110,909, 4 pages.

* cited by examiner

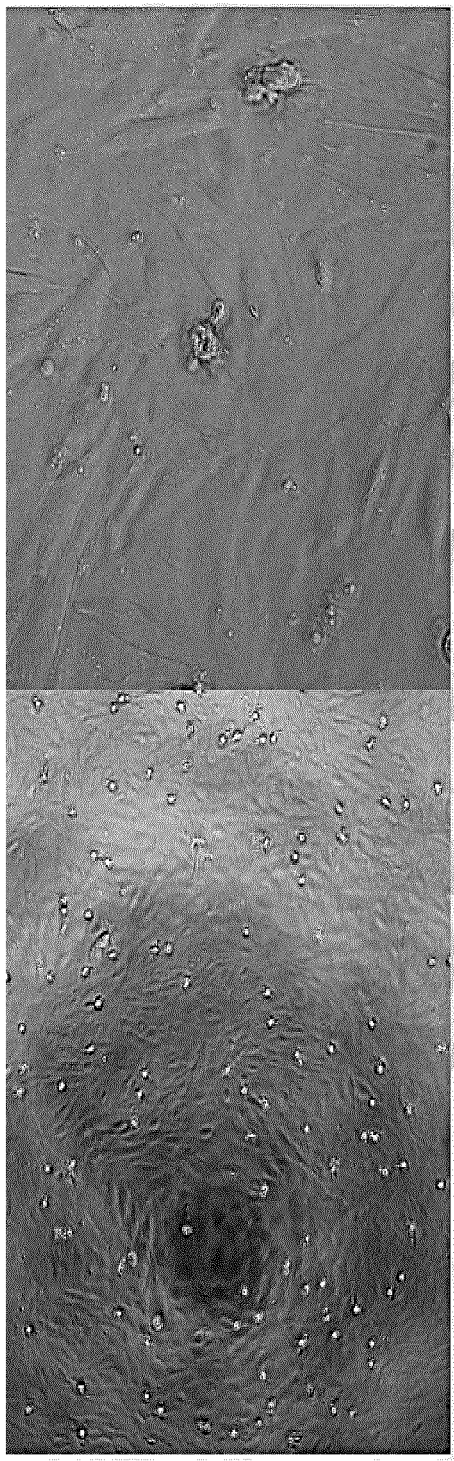
Fig. 5A
Fig. 5B
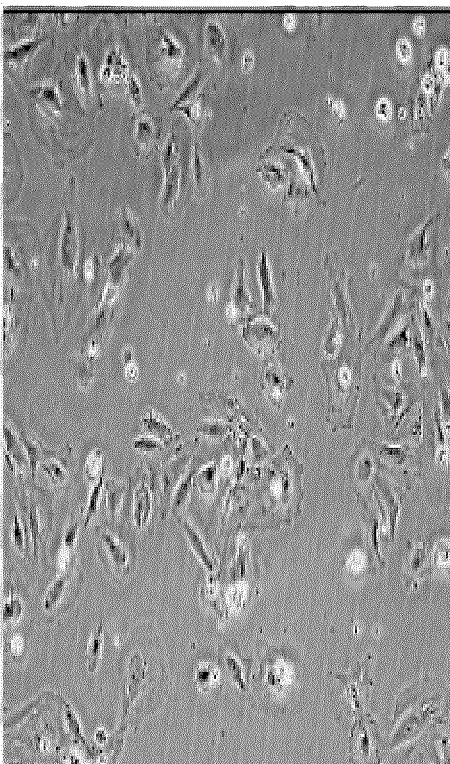
Fig. 5C

Fig. 8A
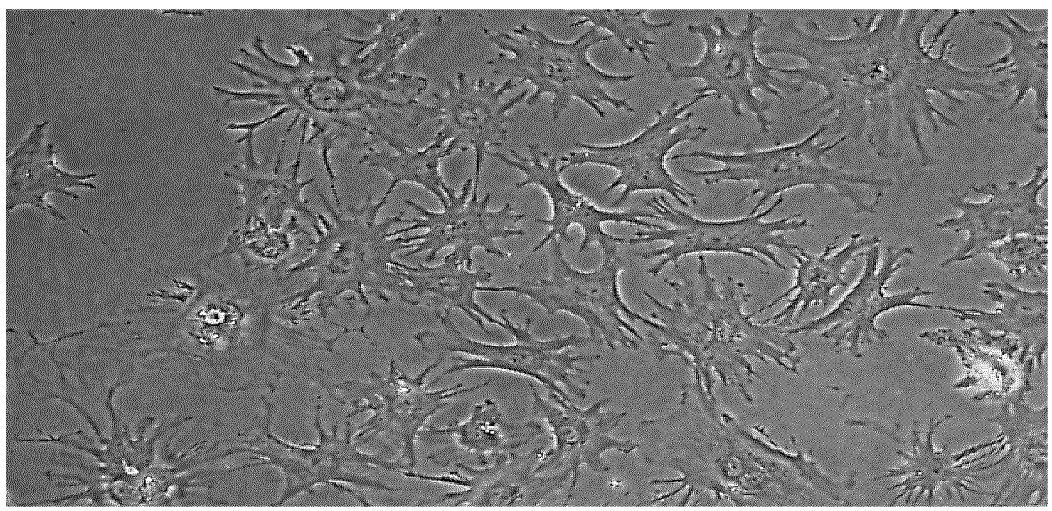
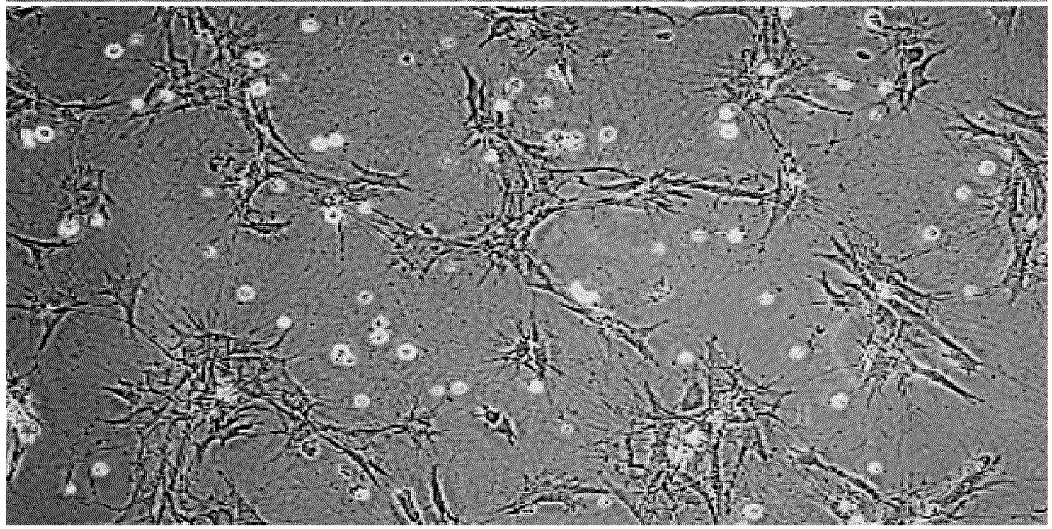
Fig. 8B

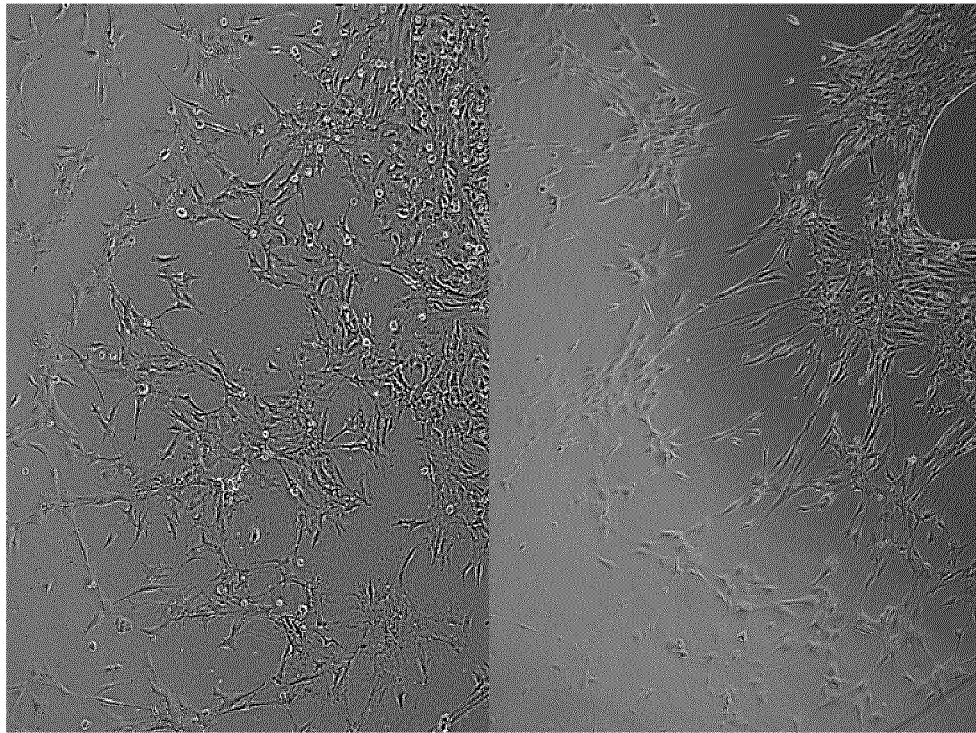
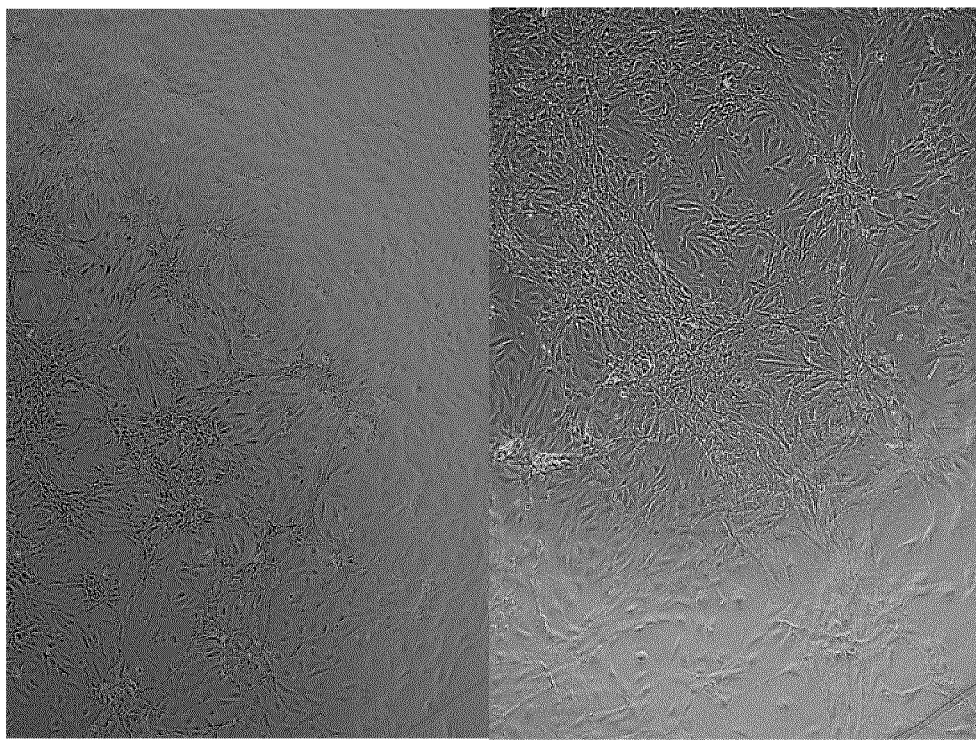
Fig. 10B
Fig. 10D
Fig. 10A
Fig. 10C

COLOSTRUM DERIVED STEM CELLS, NEURAL DIFFERENTIATION, COMPOSITIONS AND SUPPLEMENTS FOR ENHANCING MAMMALIAN HEALTH

FIELD OF THE INVENTION

The present invention relates to colostrum derived stem cells, methods for neural cell differentiation of same to treat neurological disorders or diseases in mammals, and enhancing mammalian health or the general physical condition of mammals.

BACKGROUND

Stem cells are defined as precursor cells that can divide without limit as needed and can, under specific conditions, differentiate into specialized cells. According to their source, stem cells are divided into two main groups as "embryonic" and "adult" stem cells. Embryonic stem cells are derived from blastocysts and maintain the ability to differentiate into any type of cells. Adult stem cells include all endogenous stem cells present in the adult, fetal and neonatal tissues and can differentiate into a limited number of cell lineages. Representative adult stem cells include hematopoietic stem cells (HSC) and mesenchymal stem cells (MSC) present in bone marrow.

MSC, also known as mesenchymal stromal cells, were originally isolated from bone marrow as an adherent heterogeneous cell population by in vitro culturing (1,2). MSC have been isolated from tissues including adipose tissue, dental tissues, amniotic membrane, placenta, umbilical cord and blood, endometrium, skin and breast milk (3-6). Key features of MSC are their self-renewal and multipotency. MSC have enormous therapeutic potential for tissue repair and have been shown to be capable of differentiating into multiple cell types including adipocytes, osteocytes and neural cells, to cite only a few examples (4, 7, 8). In addition to tissue repair, MSC are known to be beneficial for supporting the immune system, fighting against infection (9, 10) and enhancing the growth of organisms (11). At the onset of inflammation, injury, or infection, MSC are mobilized (from bone marrow and the other pools of MSC in the body) into circulation, are recruited to the site of the inflammation or infection, and are activated to secrete factors that mount either anti-inflammatory, or pro-inflammatory and antimicrobial responses (12-14). Importantly, MSC are not inherently immunogenic and can be used for allogeneic transplantation for any cellular therapy approaches due to the fact that they express intermediate levels of HLA class I proteins, but not HLA class II proteins (15).

There are numerous studies showing that MSC-based cellular therapies are particularly promising in the treatment of neural diseases. Many studies report that different combinations of growth factors and substances are capable of inducing differentiation of MSC into neural cells. For instance, retinoic acid and brain derived neurotrophic factor (BDNF) (8) or dimethyl sulfoxide (DMSO) (16) are known to induce neuron and astrocytes differentiation of MSC. In addition to these substances, combinations of growth factors such as epidermal growth factor (EGF), basic fibroblast growth factor (bFGF) and hepatocyte growth factor (HGF) are reported to induce differentiation of MSC into neural cells (U.S. Pat. No. 7,229,827B2). Moreover, insulin-like growth factor 1 (IGF-1) has been shown to be the one of the most important growth factors for the differentiation of both neural progenitor and MSC into neural cells (17-19).

Recently, human breast milk-derived stem cells have been shown to be capable of being differentiated into neural stem cells, then into neurons and neuroglia using the combinations of specific supplements (B27, N2) and growth factors (bFGF, EGF) with a two step culture system (20). These studies raise the possibility that MSC may be capable of cell replacement in the neurological disorders. However, these substances or methods are not applicable in clinical practice due to the toxicity of these substances, and the lengthy culture time or sophisticated culturing techniques of MSC with these substances or growth factors in vitro.

In addition to their application to treat neural diseases, MSC has been proposed to treat microbial infections due to the collective effects of their immunomodulatory and direct antimicrobial properties (US20140134140 A1). Krasnodembskaya et al. (9) indicated that bone marrow-derived MSC and their conditioned medium have beneficial effects in the treatment of sepsis induced by bacterial infection, and administration of these cells improved survival and enhanced bacterial clearance in a lung pneumonia mouse model. It was concluded that the antimicrobial effectiveness is associated with the capacity to slow bacterial growth and the ability of MSC to secrete the antimicrobial peptide LL-37. In a more recent study (10), it was shown that human MSC decreased inflammation and infection in the in vivo murine model of cystic fibrosis (CF) and that MSC derived from bone marrow and MSC derived from adipose tissue have antimicrobial and antibiotic enhancing activities against gram-positive and gram negative bacteria.

Although stem cells have been emerging in human medicine, the application of stem cell-based technologies is its infancy in livestock industry. Currently, antibiotics are widely used to prevent disease and infections as well as growth in farm animals such as pigs and dairy cows (21). However, the continued use of antibiotics in animals meant for human consumption can cause the growth of bacteria that become resistant to antibiotics. These harmful bacteria can also be passed on to humans via the food chain. The US Food and Drug Administration (FDA) and Health Canada are moving to phase out the use of some antibiotics in the livestock industry to limit the danger posed to the public by antibiotic-resistant bacteria in meat and other animal products. Therefore, new, safe and efficient strategies are needed to improve overall health and growth of livestock by preventing disease/infection without the use of antibiotics.

SUMMARY

In some embodiments, the invention is based on the development of colostrum derived stem cell populations capable of providing an antimicrobial effect and therefore useful as supplements or compositions for enhancing mammalian health, and for treating and preventing microbial contamination or infection. In some embodiments the supplements and compositions are useful in enhancing the natural immune system, thereby enhancing resistance to various diseases and improving growth, or for treating and preventing microbial contamination or infection.

In some embodiments, the invention extends to obtaining colostrum derived stem cells and inducing differentiation of these cells into neural cells using a neural progenitor medium including a mammalian cell culture medium supplemented with a casein depleted fraction of whey derived from colostrum. This supplemented medium promotes the differentiation of colostrum derived stem cells into neurons and astrocytes and enhances their growth, such that differentiation occurs in as little as two days, compared to much longer times reported in the literature.

Broadly stated, the invention provides a method of producing a population of stem cells capable of providing an antimicrobial effect, including:
  a) obtaining a population of colostrum derived stem cells; and
  b) culturing the colostrum derived stem cells to provide adherent stem cells; and including one or both of:
    i) obtaining the population of colostrum derived stem cells from a female mammal in an inflammatory state; and
    ii) culturing the colostrum derived stem cells with an inflammatory inducing agent;
to provide a population of colostrum derived stem cells capable of providing an antimicrobial effect. The population of colostrum derived stem cells having an antimicrobial effect may be formulated as compositions or supplements. In some embodiments, the population is formulated with pasteurized colostrum for use as an oral animal supplement. In some embodiments, the population is formulated for an intravenous animal supplement. In some embodiments, the population is formulated for treating or preventing microbial contamination or infection.

The invention also broadly extends to supplements or compositions for enhancing mammalian health comprising a population of colostrum derived stem cells obtained from a female mammal in an inflammatory state.

In some embodiments, the invention provides an in vitro method of inducing differentiation of stem cells, including:
  obtaining a population of colostrum derived stem cells; and
  culturing the colostrum derived stem cells in a mammalian cell culture medium supplemented with a casein depleted fraction of whey derived from colostrum to produce a population of differentiated neural cells.

In some embodiments, the invention provides a population of in vitro differentiated neural cells derived from a population of colostrum derived stem cells obtained according to the above-mentioned method.

In some embodiments, the invention provides a pharmaceutical composition comprising a population of in vitro differentiated neural cells derived from a population of colostrum derived stem cells obtained according to the above-mentioned method, together with one or more pharmaceutically acceptable carriers, excipients and diluents, for use in the treatment of a neurological disease or disorder.

In some embodiments, the invention provides a neural progenitor medium for differentiating colostrum derived stem cells, including a mammalian cell culture medium supplemented with a casein depleted fraction of whey derived from colostrum.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings.

FIGS. 1A and 1B show steps to obtain a colostrum derived stem cell population for neural cell differentiation for use in treating neurological disease or disorders in mammals. In FIG. 1A, the colostrum is collected from a healthy female mammal. In FIG. 1B, colostrum is collected from a gravid female mammal in an inflammatory state, or from a female mammal shortly after birth in an inflammatory state, wherein the inflammatory state is induced with the use of an inflammatory inducing agent such as a lipopolysaccharide toxin (LPS), with the result that an increased number of neural cells are obtained by the method of FIG. 1B compared to the method of FIG. 1A.

FIG. 2A shows the use of in vivo LPS to obtain colostrum derived stem cells supplements (oral and intravenous). FIG. 2B shows the use of in vitro LPS to obtain colostrum derived stem cell supplements (oral and intravenous). FIG. 2C shows the use of both in vivo and in vitro LPS to obtain colostrum derived stem cell supplements (oral and intravenous).

FIGS. 3A and 3B are optical micrograph of undifferentiated bovine colostrum derived stem cells, with FIG. 3A showing an example of whole cell population from bovine colostrum at day 0 (first 24 hour collection of colostrum) at 20× magnification, and FIG. 3B showing an example of cells having fibroblast-like spindle shape morphology at day 3. FIG. 3C shows typical slender MSC-like cells at day 15-20 and FIG. 3D shows big and very compact colony formation of stem cells at day 15-20 at 4× magnification using bright field through light microscopy.

FIGS. 4A and 4B show examples of cells isolated from swine and equine colostrum respectively having fibroblast-like spindle shape morphology at day 2, while FIGS. 4C and 4D show compact colony formation of stem cells from swine and equine colostrum respectively at day 6.

FIGS. 5A-5C are optical micrographs of sub-cultured swine colostrum derived stem cells, cultured with 10% FBS, as described in Example 1. FIG. 5A shows MSC-like cells at passage 3 (P3) in culture flasks at 4× magnification, while FIG. 5B shows at 20× magnification, and FIG. 5C shows 19th passage (P19) of stem cells at day 7 at 4× magnification.

FIG. 7A shows non-differentiated stem cell control while FIG. 7B shows adipogenic differentiation. In FIG. 7B, lipid droplets-unstained are shown in the left picture, while lipid droplets-stained with Oil-red appear in the right picture, through light microscopy. FIG. 7C shows osteogenic differentiation-unstained (left picture), stained with Alizarin red for calcium mineralization (right picture) through light microscopy.

FIGS. 8A-8B are optical micrographs (20×) of neural cells differentiated from swine colostrum derived stem cells at P3 for 2 days on a serum-free mammalian cell culture medium containing 10% CDF, as described in Example 5. FIG. 8A shows the morphology of astrocytes cultured with swine colostrum CDF; whereas FIG. 8B shows immature neuron like cells from swine colostrum derived stem cells cultured with bovine colostrum CDF.

FIG. 9A shows the Real-time RT-PCR results of neural marker expression in control media (colostrum derived stem cells cultured in 10% FBS), commercial media formulation (colostrum derived stem cells cultured in Mesencult-ACF Media, Stemcell Technologies Inc.), differentiated cells (colostrum derived stem cells in 10% bovine colostrum CDF and 10% swine colostrum CDF). Values showed in the histogram derive from the ratio between Nestin and GFAP and the housekeeping gene GAPDH expression. FIG. 9B shows the ELISA (enzyme-linked immunosorbent assay) results of IGF-1 concentration in both bovine colostrum and swine colostrum CDF at day 0 and day 1.

FIGS. 10A-10D are optical micrographs (4×) of swine colostrum derived stem cells at P3 exposed to bovine colostrum CDF (10%), as described in Example 7. FIG. 10A shows morphology of swine colostrum derived stem cells exposed to bovine colostrum CDF when they reached 70% confluency at day 2. FIG. 10B shows morphology of swine colostrum derived stem cells exposed to bovine colostrum CDF as soon as they were seeded before becoming adherent and before reaching confluency. FIG. 10C shows morphology of swine colostrum derived stem cells exposed to bovine colostrum CDF for 24 hours, then exposed to FBS for 48 hours. FIG. 10D shows morphology of swine colostrum derived stem cells exposed to bovine colostrum CDF for 48 hours.

DETAILED DESCRIPTION i. Definitions

Figure 1A:
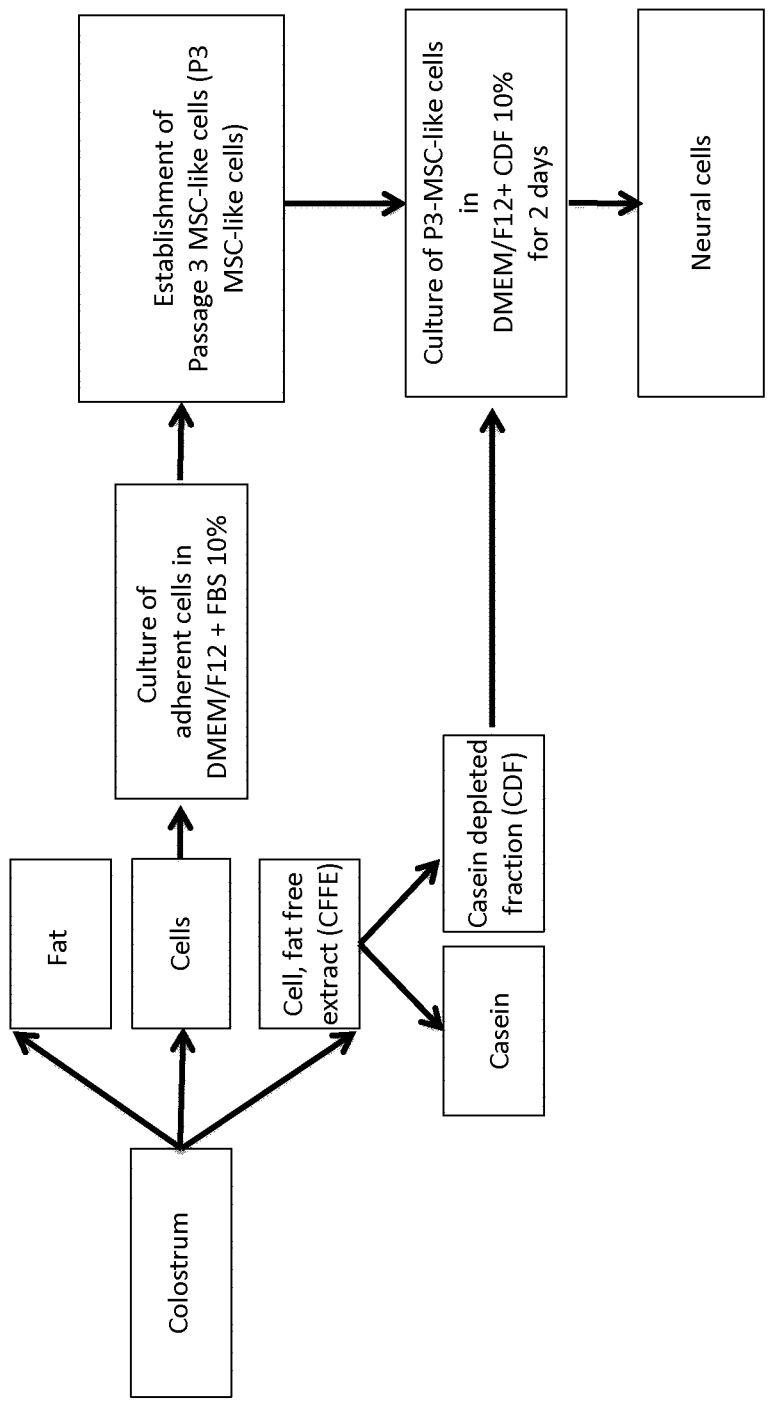
FIGS. 1A-1B is a flow charts of two embodiments of a method for neural cell differentiation using colostrum derived stem cells and colostrum CDF (casein depleted fraction of whey from colostrum).

Certain terms used herein and in the claims are defined and clarified hereinbelow.

"Stem cells" are cells that are not terminally differentiated and are therefore able to produce cells of other types. Characteristic of stem cells is the potential to develop into mature cells that have particular shapes and specialized functions, such as nerve cells, bone cells, skin cells. "Multipotent" refers to a cell capable of differentiating into cell and/or tissue types of multiple, but not all, cell lineages. Examples of multipotent stem cells are MSC and HSC.

"MSC-like cells" are colostrum derived stem cells as isolated and characterized by the inventors in accordance with techniques disclosed herein. MSC-like cells are spindle-shaped, plastic-adherent cells capable of proliferation and differentiation into adipogenic, osteogenic and neural cells, and which express MSC markers CD90 and CD105, but do not express other MSC markers including CD29, CD44 and CD73 or HSC markers CD34 and CD45. This in contrast to the accepted phenotype of MSC reported in the literature in several species (human, pig, cow, etc.), including positivity for CD90, CD105, CD29, CD44, and CD49, and negativity for CD34, CD45, CD117, CD133, and CD31 (22).

"Progenitor cell" refers to a cell that gives rise to progeny in a defined cell lineage.

"Lineage" refers to a pathway of cellular development, in which precursor or "progenitor" cells undergo progressive physiological changes to become a specified cell type having a characteristic function (e.g., nerve cell)

"Isolated" refers to a cell or a population of cells which has been separated from at least some components of its natural environment. (e.g., isolated from the body or a biological sample from the body). The biological sample can include synovial fluid, blood, colostrum or tissue.

"Obtaining" as in "obtaining the stem cell" is intended to include purchasing, isolating or otherwise acquiring the stem cell (or indicated substance or material).

"Autologous" refers to any material derived from the same individual to which it is later to be re-introduced into the individual.

"Allogeneic" refers to cells of the same species that differ genetically to the cell in comparison.

"Xenogeneic" refers to cells derived from an animal of a different species.

"In vitro" refers to an artificial environment and to processes or reactions that occur within an artificial environment. In vitro environments include, but are not limited to, test tubes and cell culture.

"In vivo" refers to the natural environment (e.g., an animal or a cell) and to processes or reaction that occur within a natural environment.

"Expansion" or "expanded" refers to the propagation of a cell or cells without terminal differentiation.

"Culture expanded population" means a population of cells whose numbers have been increased by cell division in vitro. This term may apply to stem cell populations and non-stem cell populations alike.

"Passaging" refers to the process of transferring a portion of cells from one culture vessel into a new culture vessel.

"Confluency" refers to the percentage of the area of a cell culture surface covered by adherent cells.

"Mammalian cell culture medium" is a medium that supports growth of mammalian cells. Mammalian cell culture media are known in the art. For the purposes of this invention, the mammalian cell culture medium supports the growth of colostrum derived stems cells and enhances their proliferation. Examples of mammalian cell culture medium are DMEM/F-12 (Gibco, Cat #11330-032), and Alpha MEM (Stemcell Technologies Inc.), supplemented with a serum supplement such as fetal bovine serum (FBS). The mammalian cell culture medium may also be supplemented with NEAA (non-essential amino acids), such as available from Gibco, Cat #11140050, and with antibiotics such as penicillin/streptomycin (P/S).

"Serum-free mammalian cell culture medium" is a mammalian cell culture medium without a serum supplement such as FBS, and is preferably used herein for neural cell differentiation.

"Neural differentiation medium" is a cell culture medium that supports differentiation of stem cells into neural cells (astrocytes and neurons) and enhances their further proliferation. Neural differentiation media are known in the art and generally include a mammalian cell culture medium, which may be supplemented with NEAA, and to which the growth factors IGF-1, EGF, bFGF and HGF or DMSO are added.

"Differentiation" is the process by which unspecialized or less specialized cells become more specialized to perform biological functions. For example, MSC may change from multipotent stem cells into cells committed to a specific lineage and/or cells having characteristic functions, such as neural cells.

"Neural cells" refers to the nerve-like cells including one or more of neurons, astrocytes and microglias.

"Colostrum" refers to a fluid secreted by the mammary glands of female mammals during the first few days of lactation (depending on the species, lasting for 2-4 days), containing various nutrients and protease inhibitors that keep it from being destroyed by the processes of digestion. Humans produce relatively small amounts of colostrum in the first two days after giving birth, but cows produce about nine gallons of colostrum. Cow has been accepted as a universal donor of colostrum to humans as well as other species. Colostrum contains concentrated levels of important immune factors including antibodies, immunoglobulins, cytokines and growth factors such as IGF-1, HGF, EGF, FGF (23, US20130108587A1).

"Cryopreservation" refers to preserving cells for long term storage in a cryoprotectant at low temperature. Cryoprotectants include sugars, glycols such as glycerol (e.g., 5-20% v/v in culture media), ethylene glycol, and propylene glycol, dextran, and dimethyl sulfoxide (DMSO) (e.g., 5-15% in culture media). Appropriate freezing conditions (e.g., 1-3° C. per minute) and storage conditions (e.g., between −140 and −180° C. or at −196° C. such as in liquid nitrogen) can be determined by one of skill in the art.

"Antimicrobial agent", refers to any molecule or other agent that is a biologically, physiologically, or pharmacologically active substance that acts locally or systemically in a subject to substantially reduce or inhibit microbial growth, for example, a antibacterial agent capable of reducing the proliferative capacity of bacteria. This activity of an antimicrobial agent is referred to herein as "an antimicrobial effect". The term "antibiotic" also refers to compounds capable of decreasing infectivity or virulence of bacteria.

"Enhancement," "enhance" or "enhancing" refer to an improvement in the performance of, or other physiologically beneficial increase in, a particular parameter of a cell or organism. In some embodiments, an enhanced parameter is the antimicrobial peptide secretion of MSC-like cells.

"Recruitment" or "recruited" in relation to a stem cell refers to a process whereby a stem cell in the circulatory system migrates into specific site within a tissue or organ. Recruitment/migration may be facilitated by an inflammation, infection or injury. Release of MSC is tightly controlled by systemic and local factors (such as inflammatory cytokines, hormones and growth factors). For example, cytokines granulocyte-colony stimulating factor (G-CSF) alone and a mixture of *Lycium barbarum* (Goji extract), colostrum and mushroom enhances MSC migration following their mobilization (US20130108587) However, existing methods of promoting stem cell mobilization/recruitment suffer from significant drawbacks, including high cost, unwanted side effects of G-CSF or required combinations of more than one compound etc.

A "subject" is a vertebrate, preferably a mammal, including human and non-human mammals. Mammals include, but are not limited to, primates, humans, domestic and farm animals, and zoo, sports, or pet animals such as dogs, cats, cattle, horses, sheep, pigs, rats, mice, and rabbits.

"Treatment" refers to both therapeutic treatment and prophylactic or preventative measures, wherein the object is to prevent or slow down the targeted condition, disease or disorder (collectively "ailment") even if the treatment is ultimately unsuccessful. Those in need of treatment may include those already with the ailment as well as those prone to have the ailment or those in whom the ailment is to be prevented.

"Therapeutically effective amount" and "effective amount" refers to the amount of the subject compound, composition or supplement that will elicit the biological or medical response of a tissue, system, or subject that is being sought by the researcher, veterinarian, medical doctor or other clinician. The terms "therapeutically effective amount" and "effective amount" include that amount of a compound, composition, or supplement that, when administered or fed, is sufficient to prevent development of, or alleviate to some extent, one or more of the signs or symptoms of the disorder or disease being treated, or to enhance the health or growth of the subject being treated. The therapeutically effective amount or effective amount will vary depending on the compound, composition, or supplement, the disease and its severity and the type, age, weight, etc., of the subject to be treated.

There are several broad aspects of this invention based on the inventors' research with colostrum derived stem cells, which they have characterized and refer to herein below as "MSC-like cells". One aspect provides colostrum derived stem cell populations and compositions and a method for inducing differentiation into neural cells, neurons and astrocytes. Briefly, the method includes culturing colostrum derived stem cells in a mammalian cell culture containing a casein depleted fraction (CDF) of whey derived from colostrum. The CDF is found to provide a richness of different growth factors (such as IGF-1, HGF, EGF, etc.) found in colostrum that is particularly effective in achieving neural cell differentiation in a short period of time (days rather than weeks). In addition, casein has been removed from the whey fraction of the whey for the optimal attachment and growth of colostrum derived stem cells. The differentiated neural cells have application in the treatment of neurological disorders in mammals, in which the neural cells are administered to a subject in need thereof.

In another broad aspect, stem cell populations, compositions and supplements derived from colostrum are provided for enhancing the health, immunity and the growth of mammals such as livestock, including pigs, cows and horses. This can lessen or eliminate using antibiotics.

In yet a further broad aspect, stem cell compositions are provided for reducing infection and disease in mammals such as farm animals, and for growth promotion in mammals such as farm animals. Here again, this can reduce or eliminate the use of antibiotics, and thus reduce the risk of the emergence of antibiotic-resistant pathogens. When used as feed supplements in newborn mammals or as a pharmaceutical composition (such as intravenous supplement) in older mammals, stem cell compositions offer the potential as an alternative to antibiotics for both controlling pathogens and improving growth rate.

In yet a further broad aspect, stem cell populations and compositions capable of providing an antimicrobial effect are provided for treating or preventing microbial contamination or infection, for example in medical devices or implants.

The following description includes information that may be useful in understanding the present invention. The invention can be practiced without one or more of the specific details or with other methods, components, materials etc.

ii. Isolation of Stem Cells from Colostrum

MSC-like cells are isolated from colostrum. Depending on the mammal, colostrum is produced for the first few days, although for successful MSC-like cell isolation, the colostrum is preferably collected during day 0 (i.e., in the first 24 hours), such as the first colostrum collection immediately after birth. In the case that the colostrum is transported to a processing facility remotely located from the location of the colostrum collection, it is advantageous to maintain the colostrum at a low temperature, such as at 4° C., at all times to prevent excessive bacterial growth. Freezing of the colostrum is disadvantageous to prevent cell death or denaturing of the proteins and peptides. Further, it is advantageous to process the colostrum soon after collection to ensure a high quality and quantity of the stem cells as well as the CDF of the whey fraction of the colostrum. The MSC-like cells are isolated from colostrum by centrifugation (to separate the cells from the non-cellular fat and whey fractions of the colostrum) and direct adherence method and preferably passaged up to 3 passages (P3).

Colostrum-derived MSC-like cells may be passaged, for example for 3 or 4 (P3, P4) to obtain a more homogenous and expanded cell population and a clinically useful number. The isolated MSC-like cells maintain good proliferative capacity and are able to adhere to glass and plastic surfaces that are commonly used to culture these cells in vitro. At this stage, the MSC-like cells may be used directly for cell differentiation, or they may be stored for later use, such as by cryopreservation techniques.

Figure 1B:
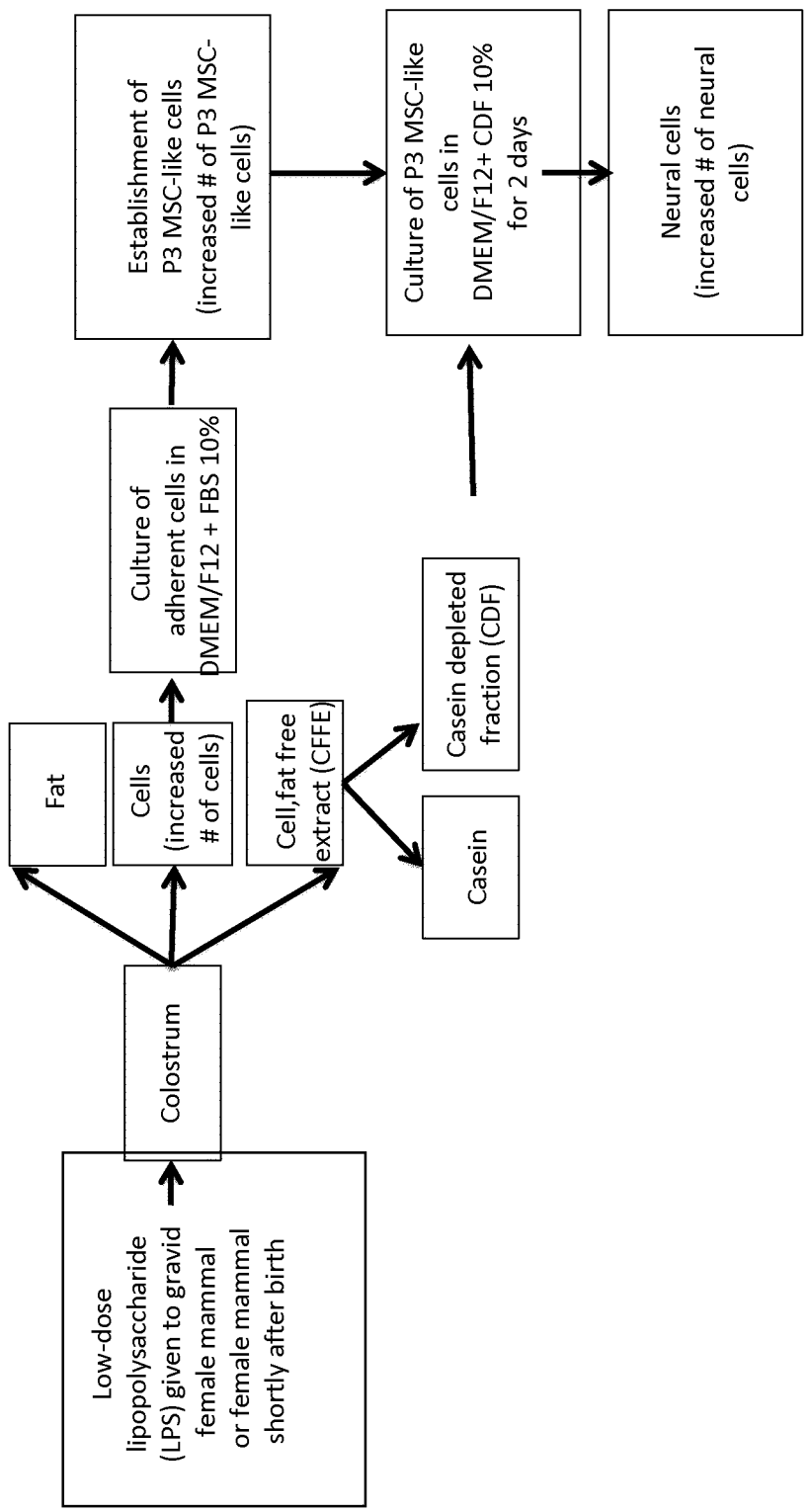

To obtain larger quantity of MSC-like cells (and neural cells in the subsequent differentiation method), colostrum can be collected from a female mammal in inflammatory state, such as a gravid female mammal or a female mammal shortly after birth. While the inflammatory state may be naturally occurring, such as from a mammal with an infection or inflammation, an inflammatory inducing agent such as low dose, for example 0.5 ng/kg, lipopolysaccharide (LPS), can be given to a gravid female mammal during pregnancy, or prior to birth, or shortly after birth, to mobilize MSC cells into the colostrum due to the inflammation (FIG. 1B). It has been reported that LPS doses as low as 0.5 ng/kg are enough to elicit an immune response, lasting no longer than 12 hours (24). In fact, the inventors observed that a large quantity of MSC-like cells are obtained from the animals with inflammation at the time of the collection of the colostrum. Larger quantity of colostrum-derived MSC-like cells give rise to enhanced amount of neural cells in the present invention.

iii. Differentiation of Colostrum Stem Cells to Neural Cells

The MSC-like stem cells isolated from colostrum are induced to differentiate into neural cells (neurons, astrocytes). Briefly, the cells are suspended in a mammalian cell culture medium supplemented with a "casein depleted fraction" (CDF) obtained from the whey fraction of the colostrum. Here again, the colostrum source for the CDF is preferably from the day0 colostrum (first 24 hours after birth). The mammalian cell culture medium is preferably serum-free. An amount of CDF included in the medium (vol/vol) is generally in the range of 2-30% or 8-20%, or about 10%. The amount used in the examples herein is 10%, however, 20% and 30% have also been found to be effective, but not significantly more effective than 10%. The MSC-like cells cultured in the medium with day0 CDF are found to differentiate into neural cells in as little as 2 days (FIG. 1A), while control medium without the CDF fraction resulted in much slower differentiation into neural cells.

The advantage of CDF supplemented media developed in the invention is provided by safe, very rapid differentiation of the cells (after only 2 days) with otherwise basic culture methods. Large quantities of neural cells are be formed after 2 weeks, with in medium supplemented with colostrum derived CDF. Evidence is presented in the literature that mesenchymal stem cells progressively differentiate into neural cells over the course of much more than a week, such as 4-8 weeks (see U.S. Pat. No. 7,229,827B2). The MSC-like cells of this invention are isolated from human colostrum, or colostrum of other mammals such as swine, bovine or equine colostrum, depending on the end recipient of the cell compositions. The advantages of using MSC-like cells obtained from colostrum are their non-invasive collection, simple isolation procedure, rapid growth, and differentiation capacity to neural cells in comparison to the other sources such as bone marrow, and cord blood. In fact, only colostrum derived MSC-like cells can be induced to differentiate into neural cells in the presence of colostrum CDF. Mesenchymal stem cells from other sources or cell types (such as cord blood- or bone marrow-derived mesenchymal stem cells or fibroblast cells) are shown not to differentiate in the presence of CDF media, as shown in Example 6. As well, as established by the inventors herein, CDF colostrum is highly advantageous for the proper culturing of colostrum-derived MSC-like cells. The inventors determined that these cells do not attach properly and grow in the colostrum containing casein fraction.

To obtain the CDF of colostrum, the colostrum is centrifuged to remove the fat fraction and the cell fraction, leaving the colostrum whey fraction. The casein can be depleted and removed by precipitating at low pH, by using precipitating agents or casein degrading enzymes, or by filtration. The casein may be precipitated by the acid method, which includes incorporating an acid, such as hydrochloric acid, acetic acid and sodium acetate) in the whey fraction of colostrum to lower the pH to less than about 4.6, such as about 4.5, at which point the casein precipitates out and may be separated from the remaining whey. The casein in the whey fraction of colostrum can also be clotted by the action of a casein degrading enzyme such as rennet. The precipitated casein (curd) and soluble proteins (whey proteins) may then be separated by centrifugation and/or filtration to obtain the CDF fraction of colostrum whey. Yet a further technique to produce CDF from the colostrum whey may include one or more steps of filtration, such as taught in WO 2017/134559.

The method used to produce the colostrum derived CDF are sufficient to produce a generally clear CDF product. In general, these methods reduce the casein to less than about 20% on a wt/vol basis, and more preferably to less than about 10% wt/vol, such as less than about 2%, but will vary with the amount of casein and the particular source of colostrum. In general, for the purposes of supplementing the mammalian cell culture medium, the casein in the CDF is sufficiently depleted such that the colostrum derived stem cells will adhere/attach during culturing in a medium supplemented with the CDF.

In some embodiments, both the MSC-like cells and the CDF are derived from day0 colostrum since the success rate of establishment of MSC-like cells and the concentrations of growth factors significantly drops 24 hours after birth. In the inventors' experience, colostrum-derived MSC-like cells did not readily differentiate into neurons using colostrum CDF obtained from day1 colostrum (obtained 24 hrs after the birth). It has been also reported that bovine colostrum supernatant (includes casein) may enhance the growth of some types of epithelial like cells, but not fibroblast cells due to the improper attachments of fibroblasts into the culture plates (25, 26).

The colostrum derived MSC-like cells (for example P3 or P4) are directly cultured in the CDF supplemented medium, or if the MSC-like cells have been cryopreserved, the cells are cultured in the CDF supplemented medium as soon as they are thawed and before the cells are allowed to become adherent or to proliferate in a medium. This is found to improve both proliferation and differentiation of neural cells at the same time (FIG. 1A, Example 7). In some embodiments, colostrum derived MSC-like cells are cultured in the colostrum CDF supplemented medium (10% CDF vol/vol), including the insulin like growth factor-1 (IGF-1) at about 9 ng/ml for 2 days or more for astrocytes, and at IGF-1 of about 32 ng/ml for 2 days or more for both astrocytes and neuron differentiation. Neural cells may be proliferated continuously for about 1 and 2 weeks without changing their media. If the medium is changed, CDF supplementation in the medium remains important to proliferate the neural cells. Large quantities of the neural cells may be formed after about 2 weeks in the CDF supplemented medium.

iv. Compositions for Neurological Disorders or Diseases

MSC-like cells, as well as neuronal cells trans-differentiated therefrom in accordance with the invention, have numerous uses, including for drug screening, diagnostics, genomics and transplantation. The mammalian colostrum-derived MSC-like cells induced with CDF supplemented medium, or the neuronal cells trans-differentiated therefrom, can be used as an active ingredient of a pharmaceutical composition for cell therapy of neurological diseases or disorders, or for therapy of spine dysfunction caused by an injury or the like. Non-limiting examples of neural diseases and disorders include Parkinson's disease, Alzheimer disease, Huntington's disease, amyotrophic lateral sclerosis, multiple sclerosis, cerebral paralysis and brain ischemia.

Compositions for treatment of neurological diseases and disorders may include pharmaceutical compositions well known to those skilled in the art in addition to the neural cells of the present invention and may be provided in the form of various formulations. The composition may be formulated into a unit dosage form suitable for administration to a subject. The composition includes an effective dose that can develop by one or several administrations. The formulation suitable for this purpose may preferably be injections. The colostrum-derived MSC-like cells induced with CDF or neuronal cells trans-differentiated therefrom may be administered in conjunction with pharmaceutically acceptable carriers, diluents and excipients. For example, a pharmaceutical preparation may be obtained by combining the cells with a carrier or media that is pharmaceutically permissible, specifically sterile water or a physiological saline solution, vegetable oil, emulsifier, suspensions, surfactant, stabilizer, excipient, vehicle, preservative, and binder. Examples of carriers and excipients are lactose, dextrose, sucrose, sorbitol, mannitol, xylitol, erythritol, maltitol, starches, gum acacia, alginates, gelatin, calcium phosphate, calcium silicate, cellulose, methyl cellulose etc.

The pharmaceutical preparation may be blended in a unit capacity format that is generally accepted as being required in a pharmaceutical application. In addition, sterilized compositions for injection can be prescribed based on known pharmaceutical applications using supporting liquids such as injectable distilled water. Such carriers or media may be added individually or in combination. In some embodiments, the carriers are cryoprotectants such as DMSO.

The composition or pharmaceutical preparation of the present invention prepared in the above manner may be administered to subjects or patients through a variety of methods, including but not limited to infusion through an injection cannula, needle or shunt, or by implantation within a carrier, but other routes of administration, are also within the scope of the invention. Administration routes may be systemic and local routes. The systematic administration may be performed by administering the pharmaceutical formulation into spinal fluid, vein or artery. In addition, the cell composition can be administered by transdermal, subcutaneous, and intramuscular introduction. Local administration may include administration to targeted portions of the central or peripheral nervous systems. Parenchymal and intrathecal sites may be used. Pharmaceutical compositions may be administered directly into a skull of a subject, for example as described in U.S. Pat. No. 7,229,827B2. The efficacy of neural cell transplantation can be assessed in an animal model (27). The cells can be derived from the recipient (autologous) or from a donor (allogeneic). Typical unit dose of the neural cells may range from $1\times10^6$ to $1\times10^9$ cells. The unit dose and frequency of the MSC-like cells induced with CDF, or trans-differentiated neural cells from MSC-like cells of the present invention, to be actually administered is determined in light of various relevant factors including the disease to be treated, the severity of the patient's symptom, the chosen route of administration, and the age, sex and body weight of the individual patient.

The compositions and method of this invention are intended for use in a mammalian subject, such as a primate or human. The method includes administering the neural cells produced by the inventive method to a subject in need thereof in a therapeutically effective amount for treating the disease or disorder.

v. Stem Cell Populations, Mammalian Supplements and Compositions to Enhance Mammalian Health In addition to neurological disorders, the present invention relates to a novel use of colostrum-derived MSC-like cells that are effective to enhance mammalian health and growth, for example as feed supplements and pharmaceutical compositions.

Mesenchymal stem cells are provided to treat microbial infections or contamination, for example associated with CF, sepsis etc., and to enhance the activity of antibiotics when combined with antibiotics. Mesenchymal stem cells have the capacity to secrete factors that are both anti-inflammatory and anti-microbial, therefore attenuating inflammation while at the same time aiding in infection resolution associated with microbial infections. In addition, mesenchymal stem cells have been shown to enhance the physical growth of animals.

The present invention encompasses a method for enhancing animal health and growth, for example by administering to, feeding or treating an animal with a colostrum-derived MSC-like cell population or composition which is capable of providing an antimicrobial effect. The ideal source of MSC for agriculture use is one that is readily available noninvasively, is obtained by simple isolation method, grows rapidly and yields large numbers of cells. In this regard, colostrum offers an alternative to bone marrow or adipose tissue (main sources for cellular therapies) due to their invasive collection procedure, slow growth of MSC obtained from these sources (up to 8-15 passages) or enzyme-base isolation procedure of adipose tissue-derived MSC (28-30).

The population of stem cells capable of providing an antimicrobial effect is provided by obtaining a population of colostrum derived stem cells and culturing the colostrum derived stem cells to provide adherent stem cells. In some embodiments the population of colostrum derived stem cells is obtained from a female mammal in an inflammatory state. In other embodiments, the population of colostrum derived stem cells is cultured with an inflammatory inducing agent.

Figure 2A:
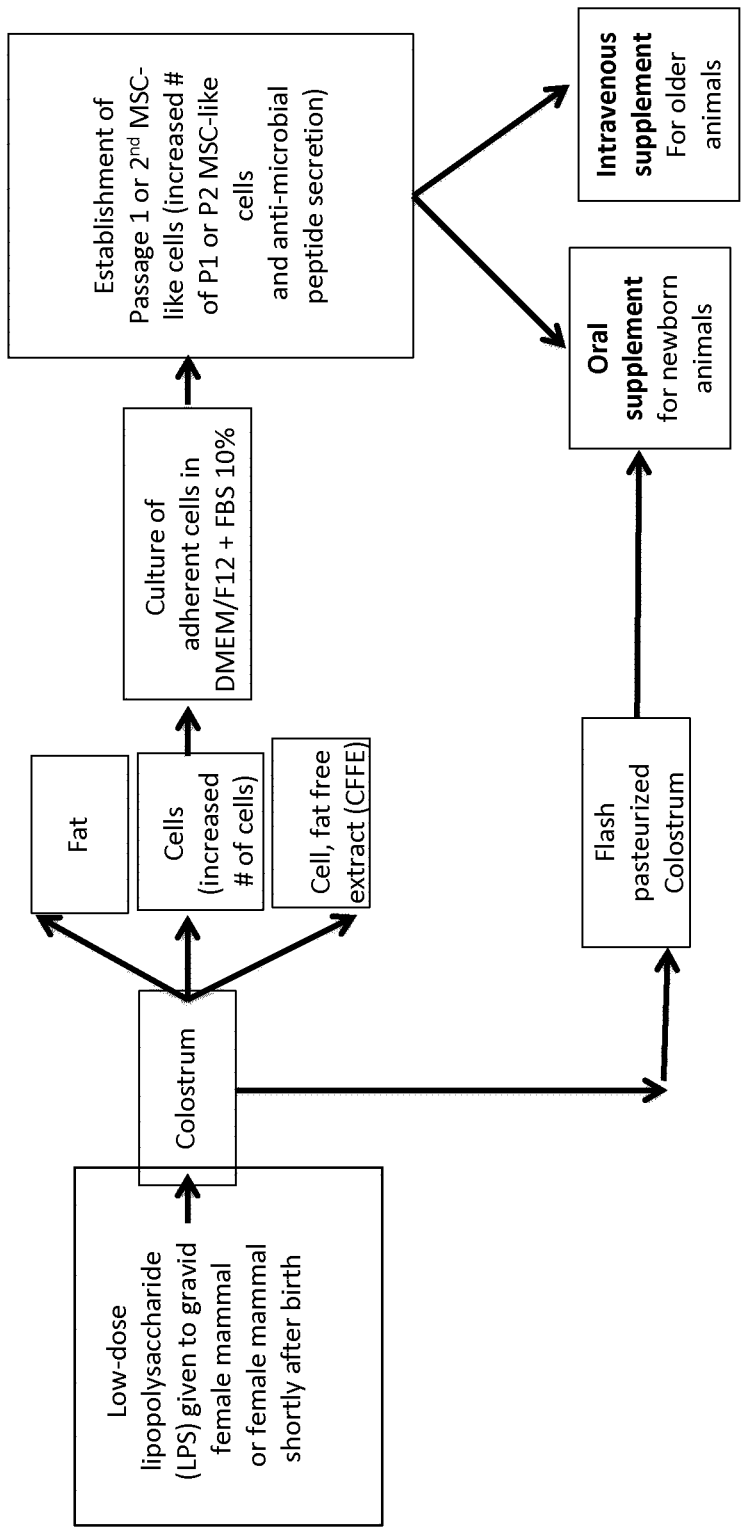
FIGS. 2A-2C are flow charts of three embodiments of a method for producing supplements or compositions for enhancing mammalian health and growth using colostrum derived stem cells from female mammals in an inflammatory state and/or by culturing the colostrum derived stem cells with an inflammatory inducing agent.
Figure 2B:
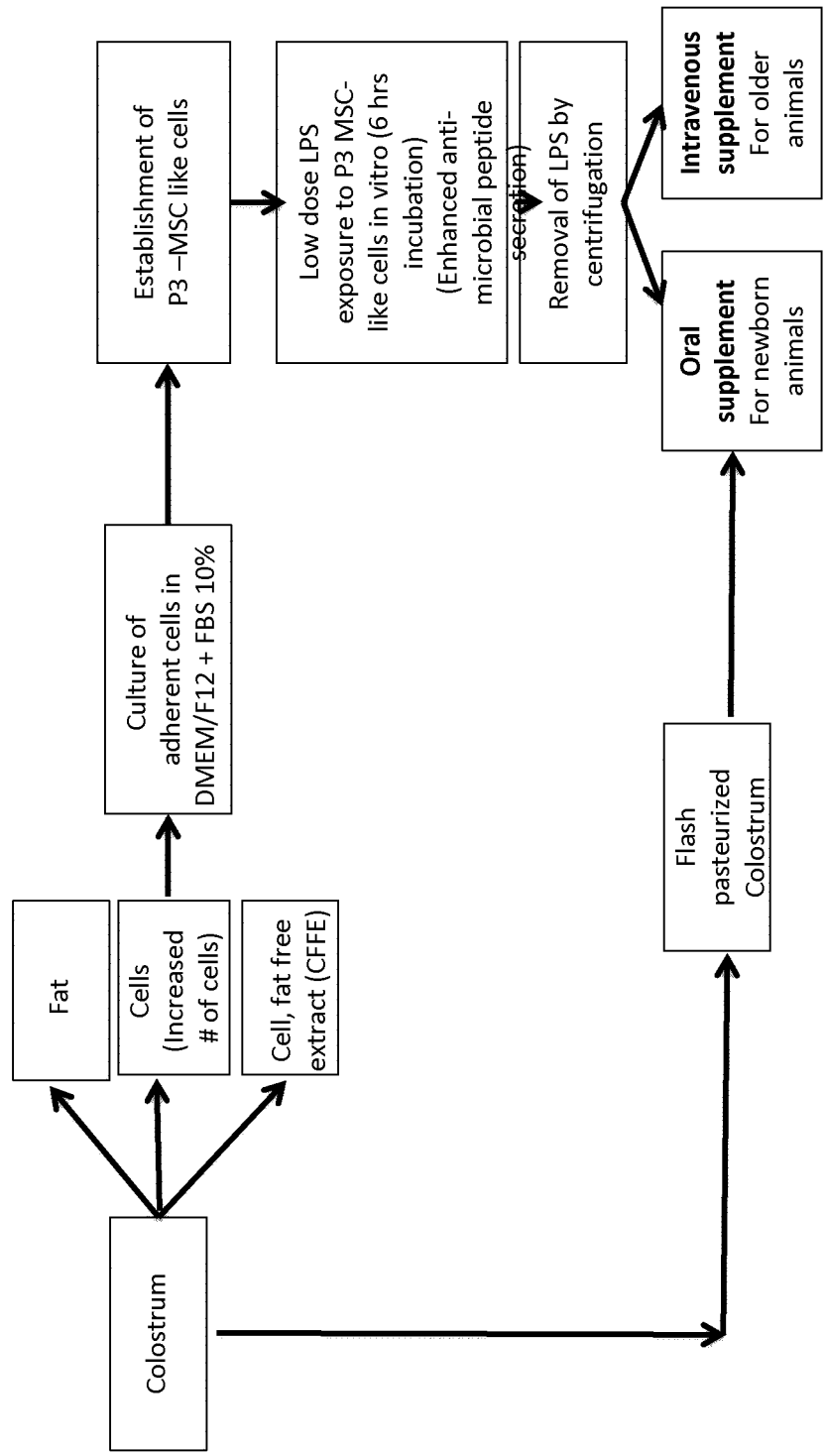
Figure 2C:
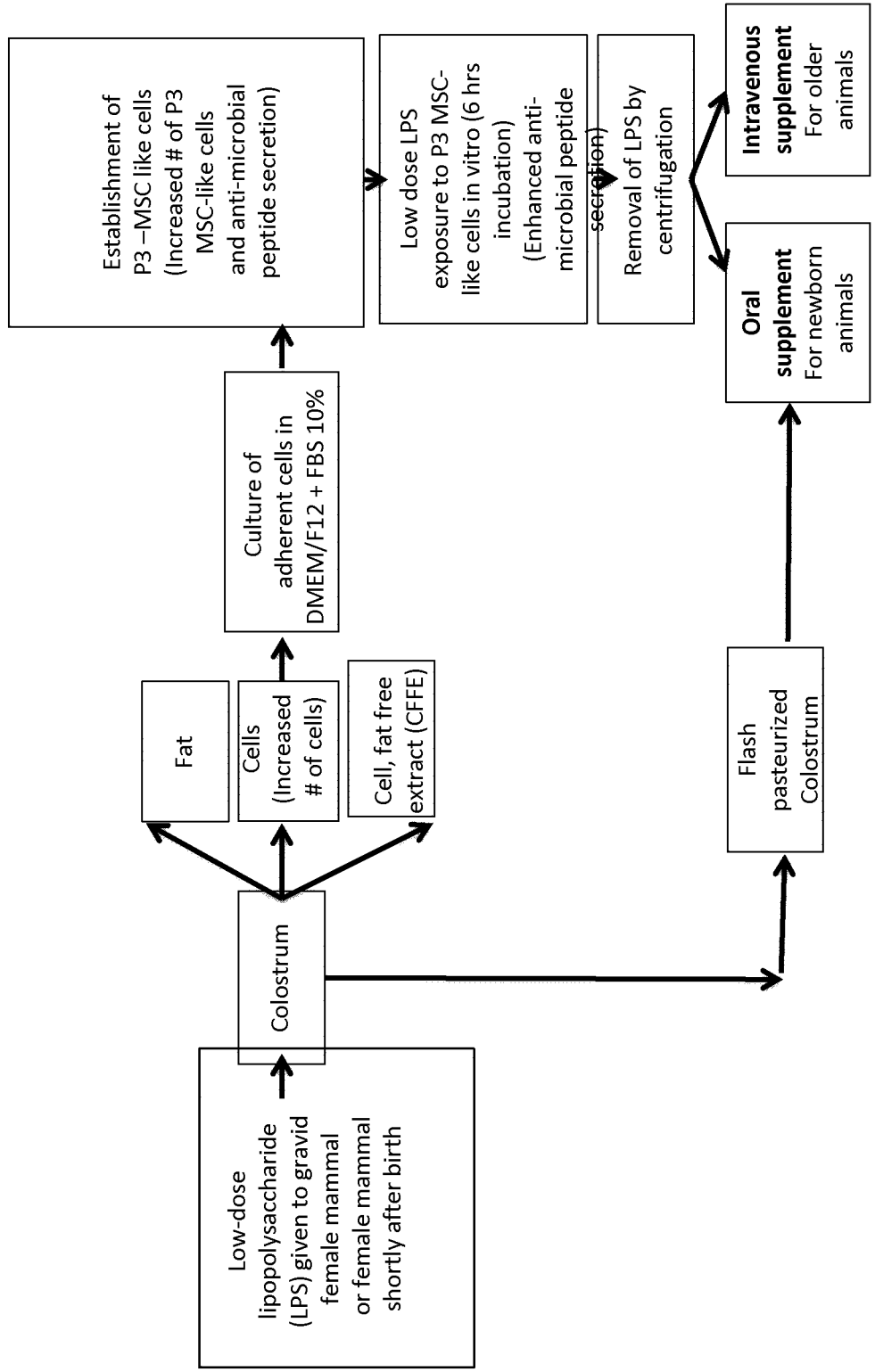

In some embodiments, colostrum is collected from a healthy gravid female or from a gravid female mammal in an inflammatory state. The inflammatory state may be naturally occurring, for example as a result of an infection or an inflammation, or the inflammatory state may be induced. For example, LPS is a bacterial endotoxin known to induce an inflammatory state in animal models. LPS is a toxic membranous product of $E.\ coli$. Thus, to induce an inflammatory state, a low-dose LPS, or other inflammatory inducing agent, is given to a gravid female mammal during the pregnancy, or before collection of colostrum, or shortly after the birth. Colostrum collected from this mammal is found to have an enhanced number of MSC-like cells, for example from day0 colostrum (FIG. 2A). In addition, MSC-like cells obtained after LPS exposure to a gravid mammal are activated to secrete antimicrobial peptide LL-37 due to inflammation in a gravid mammal. It has been demonstrated that, in MSCs, a bacterial preconditioning and/or preconditioning with LPS induces an upregulation of LL-37 (9, 10). Therefore, in some embodiments, early passages of colostrum-derived MSC-like cells such as $1^{st}$ or $2^{nd}$ passages. Alternatively, after the $3^{rd}$ passage, colostrum derived MSC-like cells are exposed to low dose LPS in vitro to activate enhanced antimicrobial secretion of these cells (FIG. 2B). Still alternatively, colostrum derived MSC-like cells are exposed to low dose LPS in vitro to activate enhanced antimicrobial secretion of these cells, in addition to initial exposure of LPS in a gravid female mammal or to a female mammal shortly after the birth (FIG. 2C).

Without being bound by same, the inventors believe that the inflammatory state as described above, such as induced by an inflammatory inducing agent such as LPS, leads to mobilization and recruitment of an enhanced number of MSC into the colostrum.

LPS may be removed from the cells by simple centrifugation. Colostrum-derived MSC-like cells may be added into flash pasteurized colostrum (example day0 colostrum) and given to a newborn animal orally as a feed supplement. In some embodiments, these colostrum-derived MSC-like cell composition may be given to a newborn mammal, for example within 24-48 hours up to one week. Colostrum-derived MSC-like cells can be combined with other cells from colostrum such as leukocytes. The cells can be derived from the recipient (autologous) or from an allogeneic or xenogeneic donor.

Compositions and supplements of the present invention may also include carriers, which are inert formulation ingredients added to compositions comprising cells, cell-free preparations or metabolites to improve recovery, efficacy, or physical properties and/or to aid in packaging and administration. Such carriers may be added individually or in combination. In some embodiments, the carriers are cryoprotectants such as glycerol.

In another aspect, the compositions of the present invention may be administered intravenously in animals older than one week as a pharmaceutical composition (FIG. 2A-2C). The pharmaceutical composition may further comprise one or more pharmaceutically acceptable inert carriers, such as preservatives, anesthetics, solubilizers, stabilizers etc. The formulation suitable for this purpose may be injections. For example, MSC-like cells may be administered as a cell suspension in a pharmaceutically acceptable liquid medium for injection. In some embodiments, the pharmaceutically acceptable liquid medium is a saline solution. The saline solution may contain additional materials such as DMSO and serum albumin.

The stem cell populations may be formulated as supplements or compositions for feeding and/or administering to mammals including humans to improve animal health or the general overall physical condition of such mammals. The compositions can be administered both for therapeutic and non-therapeutic applications. An effective amount of a composition is an amount effective to enhance the health of a mammal in comparison to a mammal that has not been administered the composition but otherwise has been administered the same diet (including feed and other compounds) as has the mammal receiving the compositions of the present invention. Indication of enhanced health include one or more of the following: increase in weight gain, which may include an increase in weight of a specific part of the mammal or an increase in overall weight; reduction in risk of mortality; increase in disease resistance; reduction in morbidity; increase in immune response; decrease in occurrence of diarrhea, increase in productivity; and/or reduction of pathogen shedding. Thus, in line with the above, embodiments of the present application are directed to non-therapeutic methods such as increasing the weight of the mammal by feeding and/or administering to the mammal a composition comprising colostrum-derived MSC-like cells.

Colostrum-derived stem cell populations capable of providing an antimicrobial effect may be formulated for treating and preventing microbial contamination or infections, for example in medical devices or implants.

The methods of the present invention may be applied to any mammals including humans. Mammals that may be treated with the composition of the present invention include farm animals; animals used for sports, recreation or for work, such as horses, including race horses; domestic household pets, including dogs, cats, birds and exotics; and zoo animals. Farm animals refer to animals raised for consumption or as food-producers. In one embodiment, the method may be applied to mammals such as swine and equine. In yet another embodiment the method may be applied to polygastric animals, such as cattle, goat and sheep, also referred to herein as ruminants. In some embodiments, the compositions of this invention may be fed to preruminants to enhance their health and, in particular, to decrease the incidence of diarrhea in these mammals.

The present invention is also illustrated by the following non-limiting examples.

Example 1—Isolation/Establishment of MSC-Like Cells from Colostrum

Figures 3A, 3B, 3C, 3D:
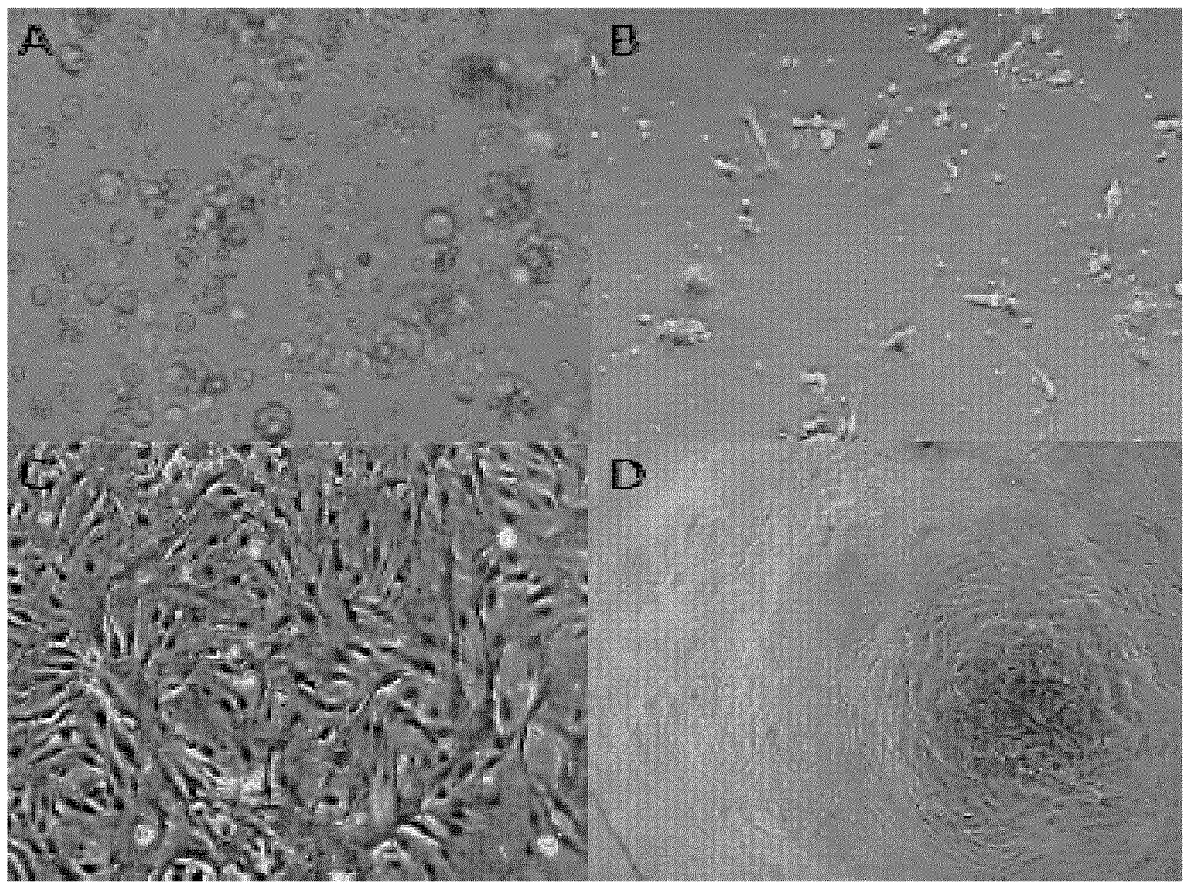
FIGS. 3A-3D are optical micrographs of bovine colostrum derived stem cells as described in Example 1.
Figure 4A:
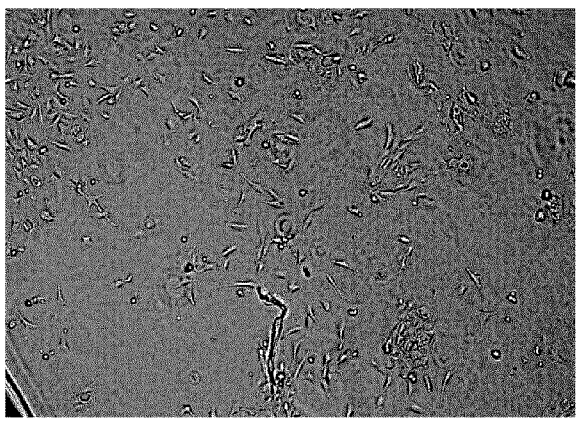
FIGS. 4A-4D are optical micrographs (4× magnification) of undifferentiated swine and equine colostrum derived stem cells as described in Example 1.
Figure 4B:
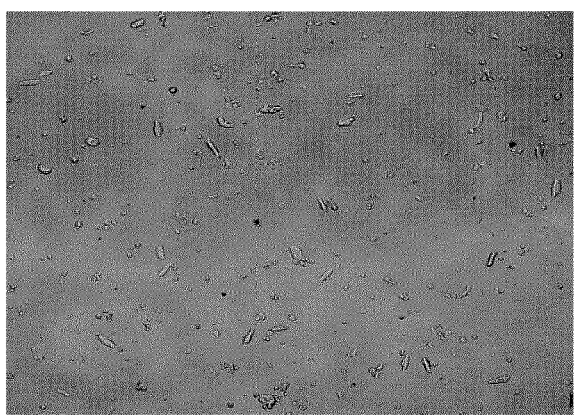
Figure 4C:
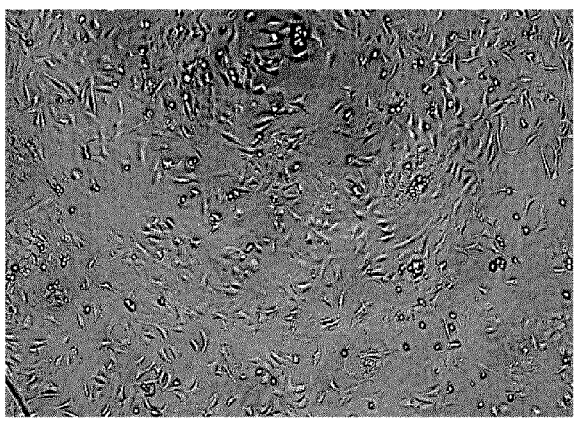
Figure 4D:
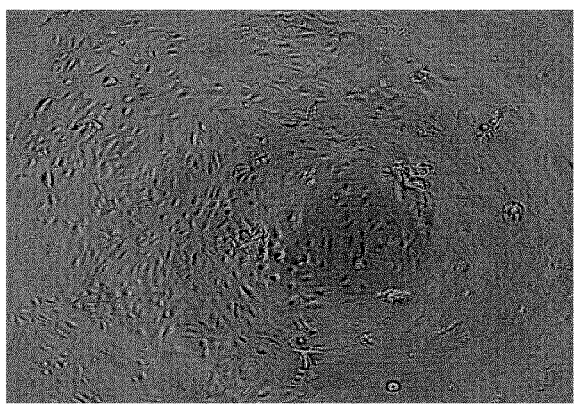

Unless otherwise indicated, amount are in vol/vol percentages. A fresh colostrum (first milk) sample collected from bovine, swine, and equine was diluted with 1:1 with HBSS (Hank's balanced salt solution) and centrifuged at 1100 rpm at 10 min. The cell pellet was washed once with HBSS with 2% anti-anti (antibiotic-antimycotic, Thermo Fisher Scientific) solution, and then 2% P/S (Penicillin/Streptomycin, Gibco-BRL) at 1100 rpm at 5 min. After cell pellet was washed twice with HBSS, the cells were seeded in 48 well plate using DMEM/F-12 (Dulbecco's Modified Eagle Medium/Nutrient Mixture F-12, Gibco-BRL) medium containing 10% FBS (fetal bovine serum, Hyclone), 1.0% NEAA, non-essential amino acids (Gibco-BRL), 1% P/S and 0.5% Plasmocin (InvivoGen) (FIG. 3A) and incubated at 37° C. under 5% $CO_2$ and 95% humidity. The cells were washed to remove non-attached cells and medium was changed at 48 h. Bovine colostrum-derived MSC-like cells attached to the culture flasks sparsely and displayed a fibroblast-like, spindle-shaped morphology during the 3 days of incubation (FIG. 3B). By the time they were 15-20 days old, typical slender MSC-like cells were observed and they formed big and very compact colonies (FIG. 3C, D). Both swine and equine colostrum-derived MSC-like cells attached to the culture flasks sparsely and displayed a fibroblast-like, spindle-shaped morphology during the 2 days of incubation (FIG. 4A, B). After 3-4 days of incubation, proliferation started and the cells gradually grew into small colonies. By the time they were 6-8 days old, colonies with different sizes increased in number (FIG. 4C, D). As growth continued, adjacent colonies interconnected with each other and a monolayer confluence was obtained after 10 days of incubation. At 70% confluency, cells were passaged using Trypsin-ethylenediaminetetraacetic (EDTA). In later passages such as passage 3 or 4 (P3, P4), MSC-like cells exhibited large, flattened or fibroblast-like morphology (FIG. 5A, B). Moreover, MSC-like cells were passaged to stop proliferating up to 19th passage (P19), showing the high clonality or immaturity of these cells (FIG. 5C). Further work was conducted with different amounts of plasmocin and MEM-NEAA (as 0.15% and 0.2% respectively). These concentrations improved the growth of the cells, indicating that growth occurs over a range of these medium components, for example 0.15-0.75% for plasmocin, and 0.2-2% for MEM-NEAA.

Example 2—Isolation/Establishment of MSC-Like Cells from Colostrum of

Female Mammals in Inflammatory State A fresh colostrum sample was also collected from 2 swine with inflammation (due to the leg edema) during the time of collection. The cells were established, passaged up to $3^{rd}$ passage by using method described in Example 1. A large amount of leukocytes as well as MSC-like cells were obtained from these animals (~4 times more cells has been collected compared to normal animals).

Example 3—Characterization of Colostrum-Derived MSC-Like Cells

Figure 6:
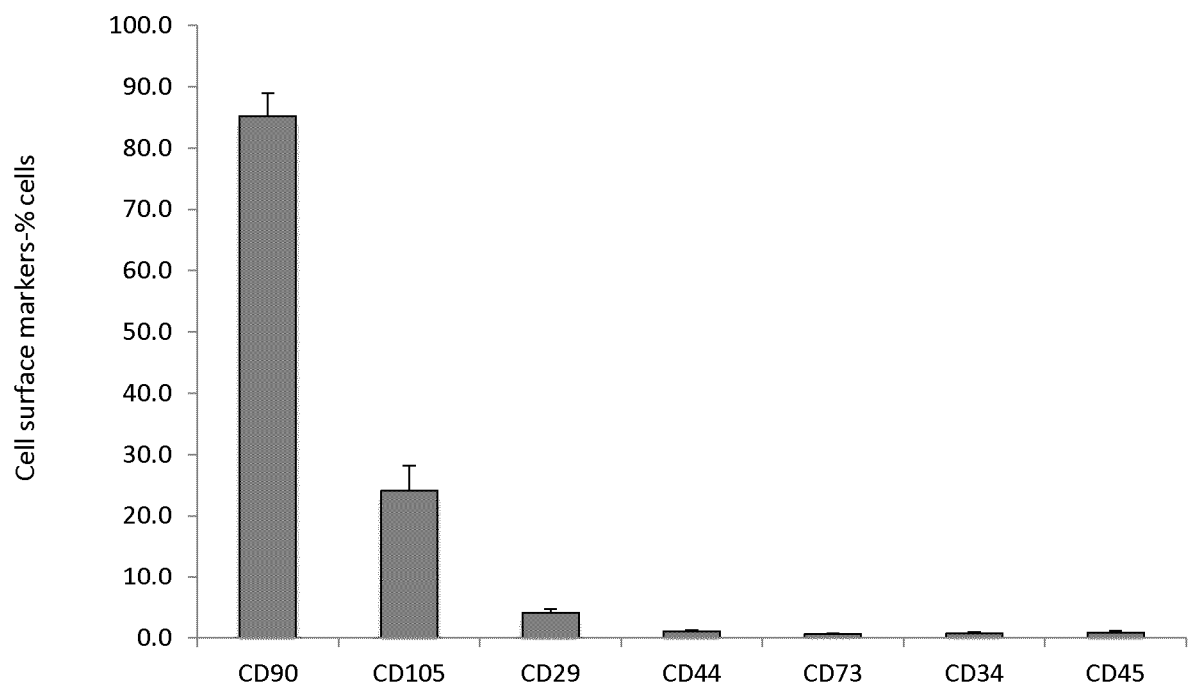
FIG. 6 derives from Example 3 and shows a representative FACS analysis (fluorescence-activated cell sorting) of swine colostrum-derived stem cells showing that the cells have characteristics of "MSC-like" cells staining positively for the MSC markers CD90 and CD105. However, the MSC-like cells do not express other MSC markers such as CD29, CD44 and CD73. In addition, the MSC-like cells are negative for the hematopoietic markers CD34 and CD45.

P4 MSC-like cells were used for the characterization studies. Seven surface markers (CD90, CD105, CD29, CD44, CD73, CD45 and CD34) of colostrum-derived MSC-like cells were assayed. Briefly, the cells were stained in HBSS supplemented with 1% BSA (bovine serum albumin) with mouse anti-human CD90-FITC, CD105-PE, CD29-PE, CD44-PE, CD73-PE, CD45-FITC, and CD34-FITC monoclonal antibodies (all from BD Biosciences). Negative control staining was performed using a FITC-conjugated mouse IgG1k isotype, a PE-conjugated mouse IgG1k isotype. After the final wash, cells were fixed in 2% paraformaldehyde prior to FACS analysis, which was performed by FACS Callibur (Becton-Dickinson, San Jose, CA). According to the FACS analysis, P3 and P4 MSC-like cells expressed MSC markers CD90 and CD105 but did not express other MSC cell surface markers such as CD29, CD44 or CD73. In addition, the MSC-like cells were found not to express CD45 or CD34, which are the typical cell surface markers of hematopoietic stem cells (see FIG. 6).

Figure 7A:
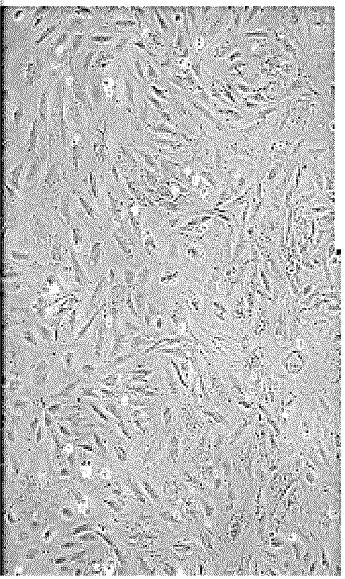
FIGS. 7A-7C are optical micrographs of differentiation properties of swine colostrum derived stem cells at P3, as described in Example 3.
Figure 7B:
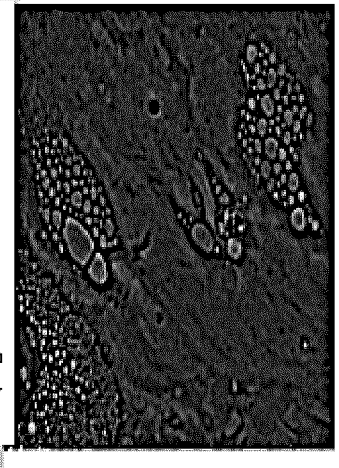
Figure 7C:
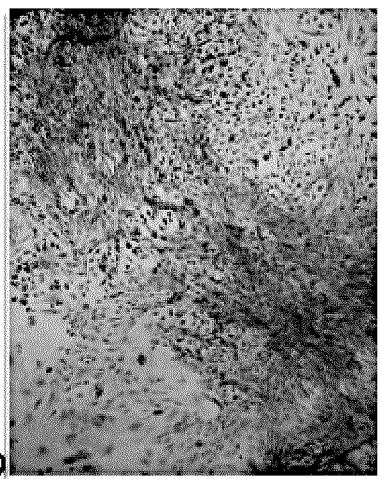
Figure 7C:
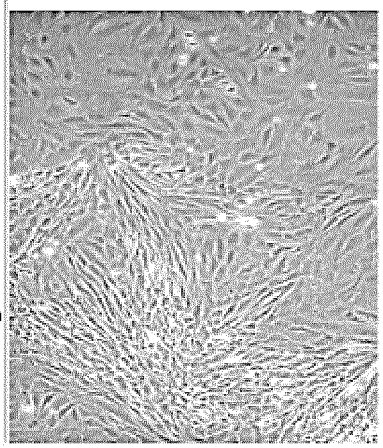

In addition to their surface markers, the differentiation potential of swine colostrum-derived MSC-like cells were evaluated. Differentiating cells are obtained by culturing MSC-like cells in a growth environment that enriches for cells with the desired phenotype, e.g. osteoblasts, adipocytes. MSC-like cells were grown in medium containing dexamethasone, ascorbic-2-phosphate and glycerol-2-phosphate (all from Sigma-Aldrich Canada) for osteogenic differentiation, whereas they were grown in medium containing isobutyl-methylxanthine (IBMX, Sigma), dexamethasone (Sigma), insulin (Invitrogen/Gibco), and indomethacin (Sigma) for adipogenic differentiation. At 4 weeks after adipogenic and osteogenic induction, cells were washed with phosphate-buffered saline and fixed and stained with Oil Red O and Alizarin red (both from Sigma) for detection of intracellular lipid droplets and calcium deposits, respectively. Cells were visualized and images were taken with the use of an inverted microscope (FSX100, Olympus). Consequently, as can be seen from FIGS. 7A, 7B, and 7C, MSC-like cells cultured and proliferated in vitro still maintain the properties of stem cells capable of differentiating into various connective tissue cells such as adipocytes and osteoblasts.

Example 4—Preparation of Casein Depleted Fraction (CDF) of Colostrum Whey

Fresh colostrum samples collected from bovine and swine were diluted 1:1 with HBSS and centrifuged at 1100 rpm at 10 min to collect the cells to establish MSC-like cells. Non-cellular portion supernatant was collected and centrifuged at 10,000 rpm for 10 min on a Sorvall centrifuge (ThermoFisher Scientific). After centrifugation, the remaining fat and cells were removed carefully from the supernatant and the bottle contents were transferred to a clean centrifuge bottle. 10 drops of concentrated rennet (Biena, Canada) were added to the supernatant, mixed for 5 min and incubated for 1 h. After a firm curd was formed, the bottle was centrifuged again at 10,000 rpm (room temperature) for 10 min to get rid off casein protein and separate the clear casein depleted fraction of whey from the curd. For further eliminating insoluble small size casein micelles from whey which may block the micro-filtration membrane filters for sterilization of colostrum whey or attachment of MSC-like cells to culture plates, the whey was filtered using membrane filters with pore size of 22 µm, 8 µm and 2.5 µm. In order to obtain sterilized CDF, the clear CDF was deployed to a series of micro-filtration steps using filters with pore sizes of 0.45 µm, 0.22 µm, and 0.1 µm to remove microorganisms. All the filtration steps were employed with a sterile filtration system (Millipore Stericup™, Fisher Canada). The sterile CDF was dispensed in 15 ml tubes and stored at −20° C. for further use.

Figure 9A:
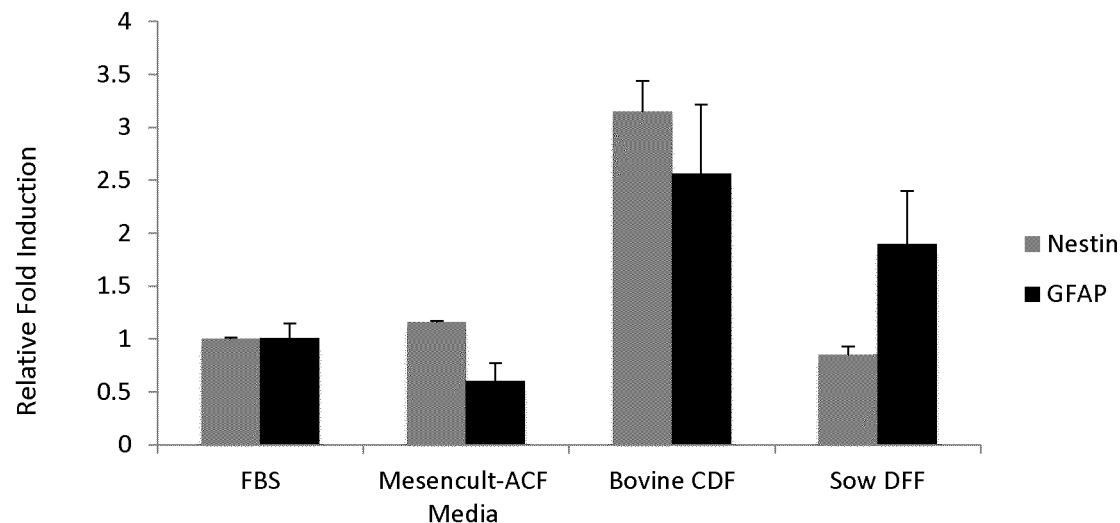
FIGS. 9A-9B relate to induction of neural gene expression in different media as described in Example 5.
Figure 9B:
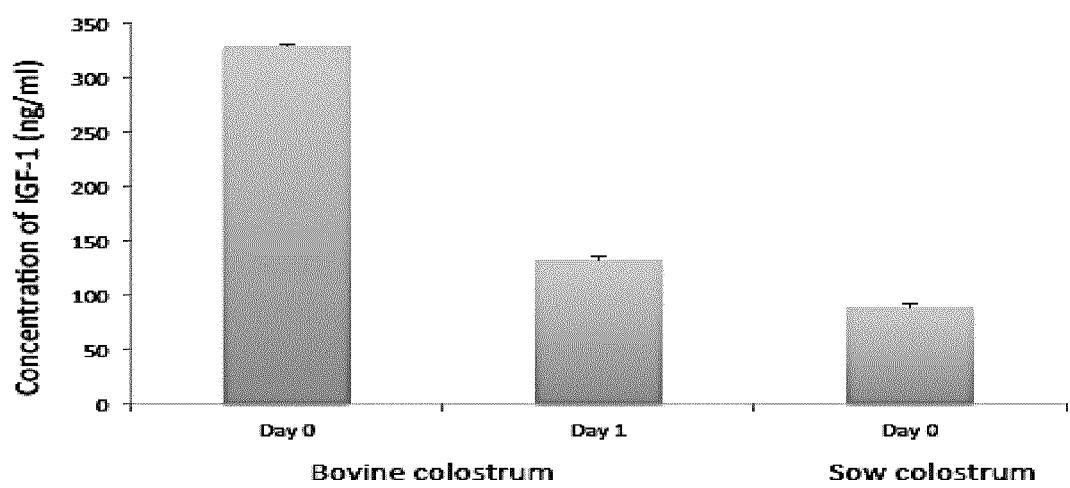

Example 5—Neural Cell Differentiation of Colostrum-Derived MSC-Like Cells with CDF In order to assess whether the MSC-like cells obtained in Example 1 differentiate into neural cells, fresh P3 swine colostrum-derived MSC-like cells were trypsinized at 70% confluency, or cryopreserved P3 swine colostrum-derived MSC-like cells were thawed, and plated in 6 well plates containing DMEM/F12 medium, 1% P/S, 1.0% non-essential amino acids and either 10% swine or bovine CDF obtained in Example 2. Cells started to show the morphological characteristics of neural cells such as astrocytes (with swine and bovine CDF) and neurons (with only bovine CDF) only after 2 days of culture (FIG. 8A, B). For the detection of astrocytes, anti-GFAP (glial fibrillary acidic protein) antibody ((R&D Systems) was administrated. It was shown that the cells were positive for GFAP and they were confirmed as astrocytes. In addition, the expression of immature neuron marker, nestin and GFAP was evaluated by quantitative real-time PCR (qPCR). Nestin and GFAP expressions were significantly high in the bovine colostrum-CDF treated group, whereas only significant GFAP expression was observed in the swine colostrum-CDF treated group (FIG. 9A). Differentiation of colostrum-derived MSC-like cells into neurons might be due to the high concentration of IGF-1 found in bovine colostrum versus swine colostrum (FIG. 9B) In addition, IGF-1 concentrations significantly dropped after 24 hours collection (FIG. 9B) and colostrum-derived MSC-like cells did not differentiate into neurons in 24 hr CDF of colostrum.

In addition, the spontaneous differentiation of some of MSC-like cells into neural cells was observed after about 4 months of culture time (passage 16$^{th}$) in the presence of the control basic media (DMEM/F12, 10% FBS, 1% P/S, 1% NEAA). As well, colostrum derived stem cells did not grow in serum-free mammalian cell culture medium (DMEM/F12, 1% P/S, 1% NEAA). Furthermore, isolated whole cell population from colostrum at day 0 showed very little growth and differentiation into astrocyte-like cells in the presence of 10% swine or bovine CDF.

Example 6—Neural Cell Differentiation of Bone Marrow- and Cord Blood-Derived MSC, and Fibroblast Cells Due to the fact that bovine colostrum is universal donor of colostrum to humans as well as other mammals and contains identical growth factors found in human colostrum such as IGF-1 as well as is sufficient for the differentiation of swine colostrum-derived MSC-like cells into neural cells, neural cell differentiation of both human cord blood- and bone marrow-derived MSC and human fibroblast cells were tested in a medium containing either bovine or swine CDF. None of these cells grew, proliferated or differentiated into neural cells using either bovine or swine CDF.

Example 7—Exposure of Colostrum-Derived MSC-Like Cells to CDF at Different Conditions This example assesses whether the MSC-like cells obtained in Example 1 differentiate into neural cells when they reached to their confluency or their medium is changed (into 10% FBS without CDF) after 24 hr initial incubation with bovine colostrum CDF (10%). Fresh P3 swine colostrum-derived MSC-like cells were trypsinized at 70% confluency and plated in 6 well plates containing DMEM/F12 medium, 1% P/S, 1% non-essential amino acids and 10% bovine CDF, 10% FBS, or first bovine 10% CDF (24 hr) then 10% FBS. Cells were incubated 2 days and analyzed. Although some swine colostrum-derived MSC-like cells differentiated into neural cells (10%-20%) when they reached 70% confluency, they did not fully differentiate, and undifferentiated swine colostrum-derived MSC-like cells were mostly observed (90%-80%) (FIG. 10 A, B). In addition, changing media from serum-free mammalian cell culture media into FBS media blocked the terminal differentiation of these cells into neural cells, emphasizing that the cells did not differentiate into neural cells as efficiently as when the when the media was supplemented with CDF at a time before the cells became adherent or proliferated. Thus, it is preferable to culture the cells in CDF supplemented media before the cells become adherent or proliferate in a medium, and to continue culturing in the CDF supplemented medium for at least 48 hrs (see FIG. 10 C, D) in order to obtain efficient neural differentiation of the MSC-like cells.

Example 8—Bacterial Culture and Antimicrobial Assay

Bacterial culture preparation and antimicrobial assay were performed as previously described (9) with modifications. Briefly, Gram-positive, *Staphylococcus aureus* (*S. aureus*) were used for this experiment. *S. aureus* colonies were transferred from glycerol stocks kept at −80° C. to TSA (trypticase soy agar) plates and incubated for 24 h at 37° C. Next day, two colonies from each agar plate were cultured into sterile flasks containing liquid TSB (trypticase soy broth) medium (Difco BD, MD) and were grown overnight under gyratory shaking at 37° C.

After 18 h of growth, both microorganisms were harvested by centrifugation, washed once with 0.1 M (pH 7) potassium phosphate buffer (PBS), re-suspended in PBS, and the optical density (OD at $\lambda=600$ nm) of each suspension was measured. Dilutions of each microbial suspension were prepared and the correlation between the OD600 and number of CFU (colony forming units) established. Number of CFU was calculated according to the following equation: OD600=0.5 corresponds to $2\times10^9$ CFU/ml.

Figure 11:
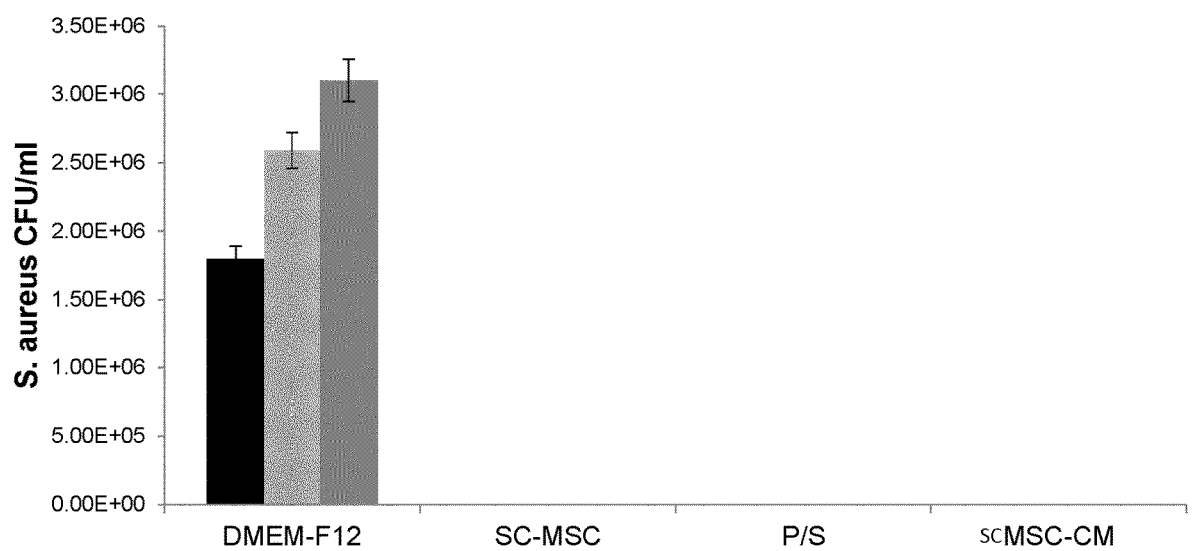
FIG. 11 demonstrates the antimicrobial activity for swine colostrum derived stem cells from a gravid mammal in an inflammatory state as described in Example 8. The Figure shows the growth of gram-positive bacteria *S. aureus* (assessed by CFU counts) exposed to swine colostrum derived stem cells, conditioned media obtained from swine colostrum derived stem cells previously exposed *S. aureus*, and antibiotics (penicillin/streptomycin).

Assessment of direct inhibition of bacterial growth by MSC-like cells or their conditioned medium (CM) (obtained from MSC-like cells exposed *S. aureus*) was done by counting CFU. P4 MSC-like cells obtained from a gravid female mammal in an inflammatory state (see Example 2) at a density of $2\times10^5$ cells per well in DMEM-F12 supplemented with 5% FBS were infected with each of the 500, 1000 and 2000 CFU of *S. aureus* and incubated for 6 hours in a humidified incubator supplemented with 5% $CO_2$. At each specific time, aliquots of the culture medium were taken from each well, serially diluted with sterile PBS, and plated on TSA-agar plates. CFU for each experimental condition were counted after 24 h incubation at 37° C. and analyzed under the microscope. To evaluate the potential of MSC-like cells or their CM compared to antibiotics, *S. aureus* were grown in the presence of 1% antibiotics penicillin and streptomycin (P/S) for 6 hours in a humidified incubator supplemented with 5% $CO_2$. Consequently, MSC-like cells and their CM significantly inhibited bacterial growth compared with control medium (DMEM/F12) after 6-hour co-incubation. In addition, similar inhibitory effect was detected in the positive control group, 1% antibiotics penicillin and streptomycin (P/S) with *S. aureus* (FIG. 11).

INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention can be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, a size range, or a composition or concentration range, all intermediate ranges and sub-ranges, as well as all individual values included in the ranges given are intended to be included in the disclosure. It will be understood that any sub-ranges or individual values in a range or sabring that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

Patent Documents

U.S. Pat. No. 7,229,827B2, issued Jun. 12, 2007 to Pharmicell Co. Ltd., "Method for differentiating mesenchymal stem cells into neural cells".

US Patent Publication No. 20140134140A1, published May 15, 2014 to Case Western Reserve University, "Mesenchymal stem cell compositions for the treatment of microbial infections".

PCT Patent Publication WO 2017/134559, published Aug. 10, 2017 to Innomed S.A., "Extraction process from colostrum".

US Patent Publication No. 20130108587A1, published May 2, 2013 to Stemtech International Inc., "Methods and compositions for enhancing stem cell mobilization".

Non-Patent Documents

1. Friedenstein A J et al., "Precursors for fibroblasts in different populations of hematopoietic cells as detected by the in vitro colony assay method", Exp. Hematol, 1974, Vol 2, No 2, pp. 83-92.
2. Whitfield M J et al., "Onset of heterogeneity in culture-expanded bone marrow stromal cells", Stem Cell Res, 2013, Vol. 11, No. 3, pp. 1365-1377.
3. Marquez-Curtis L A et al., "Mesenchymal stromal cells derived from various tissues: Biological, clinical and cryopreservation aspects", Cryobiology, 2015, Vol. 71, No. 2, pp. 181-197.
4. Patki S et al., "Human breast milk is a rich source of multipotent mesenchymal stem cells", Hum Cell, 2010, Vol. 23, No. 2, pp. 35-40.
5. Fan Y et al., "Unravelling the mystery of stem/progenitor cells in human breast milk", PLoS One, 2010, Vol. 5, No. 12, pp. e14421.
6. Sani M et al., "Origins of the breast milk-derived cells; an endeavor to find the cell sources", Cell Biol Int, 2015, Vol. 39, No. 5, pp. 611-618.
7. Ullah I et al., "Human mesenchymal stem cells—current trends and future prospective", Biosci Rep, 2015, Vol. 35, No. 2, pp. e00191.
8. Anghileri E et al., "Neuronal differentiation potential of human adipose-derived mesenchymal stem cells", Stem Cells Dev, 2008, Vol. 17, No. 5, pp. 909-916.
9. Krasnodembskaya A et al., "Antibacterial Effect of Human Mesenchymal Stem Cells Is Mediated in Part from Secretion of the Antimicrobial Peptide LL-37", Stem Cells, 2010, Vol. 28, No. 12, pp. 2229-2238.
10. Sutton M T et al., "Antimicrobial Properties of Mesenchymal Stem Cells: Therapeutic Potential for Cystic Fibrosis Infection, and Treatment", Stem Cells Int, 2016, 2016: 5303048.
11. Abd Allah S H et al., "Breast milk MSCs: An explanation of tissue growth and maturation of offspring", IUBMB Life, 2016, Vol. 68, No. 12, pp. 935-942.
12. Bernardo M E et al., "Mesenchymal stromal cells: sensors and switchers of inflammation", Cell Stem Cell, 2013, Vol. 13, No. 4, pp. 392-402.
13. Eggenhofer E et al., "The Life and Fate of Mesenchymal Stem Cells", Front Immunol, 2014, Vol. 19, No. 5, pp. 148.
14. Alcayaga-Miranda F et al., "Antimicrobial Activity of Mesenchymal Stem Cells: Current Status and New Perspectives of Antimicrobial Peptide-Based Therapies", Front Immunol, 2017, Vol. 8, pp. 339.
15. Le Blanc K and Ringden O, "Immunobiology of human mesenchymal stem cells and future use in hematopoietic stem cell transplantation", Biol Blood Marrow Transplant, 2005, Vol. 11, No. 5, pp. 321-34.
16. Woodbury D et al., "Adult rat and human bone marrow stromal cells differentiate into neurons", J Neuro Res, 2000, Vol. 61, No. 4, pp. 364-370.
17. Hsieh J et al., "IGF-I instructs multipotent adult neural progenitor cells to become oligodendrocytes", J Cell Biol, 2004, Vol. 164, No. 1, pp. 111-122.
18. Huat T J et al., "IGF-1 enhances cell proliferation and survival during early differentiation of mesenchymal stem cells to neural progenitor-like cells", BMC Neurosci. 2014; 15:91.
19. Zhao L et al., "Effects of IGF-1 on neural differentiation of human umbilical cord derived mesenchymal stem cells", Life Sciences, 2016, Vol. 151, No. 15, pp. 93-101.
20. Hosseini S M et al., "Differentiation of human breast-milk stem cells to neural stem cells and neurons", Neurol Res Int, 2014; 2014:807896.
21. Landers T F et al., "A Review of Antibiotic Use in Food Animals: Perspective, Policy, and Potential", Public Health Rep, 2012, Vol. 127, No. 1, pp. 4-22.
22. Boxall S A and Jones E, "Markers for characterization of bone marrow multipotential stromal cells", Stem Cells Int, 2012, Vol. 2012, 975871.
23. Thapa B R, "Health factors in colostrum", Indian J Pediatr, 2005, Vol. 72, No. 7, pp. 579-581.
24. Dillingh M R et al., "Characterization of inflammation and immune cell modulation induced by low-dose LPS administration to healthy volunteers", Journal of Inflammation, 2014, 11:28.
25. Steimer K S et al., "The serum-free growth of cultured cells in bovine colostrum and in milk obtained later in the lactation period", J Cell Physiol, 1981, Vol. 109, No. 2, pp. 223-234.
26. Steimer K S and Klagsbrun M, "Serum-free growth of normal and transformed fibroblasts in milk: differential requirements for fibronectin", J Cell Biol, 1981 Vol. 88, No. 2, pp. 294-300.
27. McDonald J W, et al., "Transplanted embryonic stem cells survive, differentiate and promote recovery in injured rat spinal cord", Nat Med, 1999, Vol. 5, No. 12, pp. 1410-1413.
28. Banfi A et al., "Proliferation kinetics and differentiation potential of ex vivo expanded human bone marrow stromal cells: Implications for their use in cell therapy", Exp Hematol, 2000, Vol. 28, No., pp. 707-715.
29. Muraglia A et al., "Clonal mesenchymal progenitors from human bone marrow differentiate in vitro according to a hierarchical model", J Cell Sci 2000, Vol. 113, pp. 1161-1166.
30. Yarak S and Okamoto O K, "Human adipose-derived stem cells: current challenges and clinical perspectives", An Bras Dermatol, 2010, Vol. 85, No. 5, pp. 647-656.

The invention claimed is:

1. A method of producing a population of stem cells capable of providing an antimicrobial effect, comprising:
   a) obtaining a population of colostrum derived stem cells; and
   b) culturing the colostrum derived stem cells to provide adherent stem cells; and including one or both of:
      i) obtaining the population of colostrum derived stem cells from a female mammal in an inflammatory state; and
      ii) culturing the colostrum derived stem cells with an inflammatory inducing agent;
   to provide a population of adherent colostrum derived stem cells capable of providing an antimicrobial effect.

2. The method of claim 1, wherein the population of adherent colostrum derived stem cells are passaged for two or more passages.

3. The method of claim 1, wherein the population of colostrum derived stem cells in step a) is obtained from a female mammal in an inflammatory state in accordance with step i), and wherein performing step i) provides a greater number of adherent colostrum derived stem cells than are produced in culture without performing step i).

4. The method of claim 2, wherein the population of colostrum derived stem cells in step a) is obtained from colostrum by centrifugation to separate cells from non-cellular portions of the colostrum, wherein the cells are then cultured to obtain the population of adherent colostrum derived stem cells, and wherein the population of adherent colostrum derived stem cells are isolated.

5. The method of claim 3, wherein the population of colostrum derived stems cells is obtained from the female mammal in an induced inflammatory state.

6. The method of claim 5, wherein the induced inflammatory state is achieved by administering an inflammatory inducing agent to the female mammal in a gravid state or to the female mammal shortly after giving birth, in advance of collecting colostrum.

7. The method of claim 6, wherein the inflammatory inducing agent is a lipopolysaccharide.

8. The method of claim 2, wherein the population of adherent colostrum derived stem cells is cultured with the inflammatory inducing agent, and the inflammatory inducing agent is thereafter removed from the culture.

9. The method of claim 8, wherein the inflammatory agent is a lipopolysaccharide.

10. The method of claim 1, wherein the population of colostrum derived stem cells is derived from one or more of human, bovine, equine or swine colostrum.

11. The method of claim 2, wherein the population of adherent colostrum derived stem cells, or conditioned medium derived from the population of adherent colostrum derived stem cells, capable of providing an antimicrobial effect, is isolated and preserved.

12. The method of claim 11, wherein preserving is by cryopreservation.

13. The method of claim 1, wherein the population of adherent colostrum derived stem cells capable of providing an antimicrobial effect is formulated with pasteurized colostrum for use as an oral animal supplement.

14. The method of claim 1, wherein the population of adherent colostrum derived stem cells capable of providing an antimicrobial effect is formulated for an intravenous animal supplement.

15. The method of claim 1, wherein the population of adherent colostrum derived stem cells, or conditioned medium derived from the population of adherent colostrum derived stem cells, capable of providing an antimicrobial effect is formulated for treating or preventing microbial contamination or infection.

16. The method of claim 2, wherein the population of colostrum derived stem cells are derived from colostrum collected from a mammal within 2-4 days of giving birth, or within 24 hours of giving birth.

17. The method of claim 2, wherein the population of adherent colostrum derived stem cells are mesenchymal stem cell (MSC)-like cells capable of expressing the markers CD90 and CD 105, but which do not express the markers CD29, CD44, CD73, CD45 and CD34, when assayed with monoclonal antibodies CD90-FITC, CD105-PE, CD29-PE, CD44-PE, CD73-PE, CD45-FITC and CD34-FITC.

\* \* \* \* \*